United States Patent [19]

Hamby et al.

[11] Patent Number: 5,198,426
[45] Date of Patent: Mar. 30, 1993

[54] RENIN INHIBITORS CONTAINING C-TERMINAL DIHYDROXY AMIDES

[75] Inventors: James M. Hamby, Livonia; John C. Hodges; Sylvester Klutchko, both of Ann Arbor, all of Mich.

[73] Assignee: Warner-Lambert Company, Morris Plains, N.J.

[21] Appl. No.: 441,704

[22] Filed: Dec. 4, 1989

Related U.S. Application Data

[63] Continuation-in-part of Ser. No. 292,575, Dec. 30, 1988, abandoned.

[51] Int. Cl.$^5$ ............... A61K 37/02; C07K 5/06
[52] U.S. Cl. ............................. 514/19; 514/18; 530/330; 530/331; 544/139; 544/145; 544/159; 544/370; 544/374; 544/383; 548/215; 548/314.7; 548/315.1; 548/338.1; 548/338.5; 548/312.7; 548/312.4
[58] Field of Search ............ 514/19, 18; 530/330, 530/331; 544/139, 145, 159, 370, 374, 383; 548/215, 300

[56] References Cited

U.S. PATENT DOCUMENTS

| 4,725,584 | 2/1988 | Luly et al. | 514/19 |
| 4,853,463 | 8/1989 | Iizuka et al. | 530/323 |
| 4,863,905 | 9/1989 | Hudspeth et al. | 514/19 |

FOREIGN PATENT DOCUMENTS 0202577 11/1986 European Pat. Off. .
0229667 7/1987 European Pat. Off. .
0273893 7/1988 European Pat. Off. .

OTHER PUBLICATIONS

Plattner et al. *J. Med. Chem.*, 1988, 31(12), pp. 2277–2288.
Denkewaller et al. *Progress In Drug Research* vol. 10, 1966, pp. 510–512.
Burger, *Medicinal Chemistry*, 1960, pp. 565–571, 578–581, 600–601.
Tet. Lett., vol. 29, No. 32, pp. 3923–3926, 1988 Metternich et al, "New Diastereoselective Synthesis of Novel Chiral ψ-(Aminoalkyl)-α-Hydroxy-ψ-Lactones and Their Application for the Synthesis of Renin Inhibitors".
Journal of Medicinal Chemistry, vol. 31, No. 4, Apr. 1988, pp. 701–704.

*Primary Examiner*—Lester L. Lee
*Attorney, Agent, or Firm*—Elizabeth M. Anderson

[57] ABSTRACT

The invention concerns novel renin-inhibitory peptides which are useful for treating renin-associated hypertension, congestive heart failure, hyperaldosteronism, glaucoma and diseases caused by retroviruses. Processes for preparing the peptides novel intermediates in the processes, compositions containing them, and methods of using them are included. Also included is a diagnostic method which uses the compounds to determine the presence of renin-associated hypertension, or hyperaldosteronism.

7 Claims, No Drawings

RENIN INHIBITORS CONTAINING C-TERMINAL DIHYDROXY AMIDES

CROSS REFERENCE TO RELATED APPLICATION

This application is a continuation-in-part of U.S. Ser. No. 292,575, filed Dec. 30, 1988, and now abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension, congestive heart failure, and hyperaldosteronism.

The present invention concerns novel peptides which inhibit renin. It also concerns pharmaceutical compositions containing these novel peptides, methods of treating renin-associated hypertension, congestive heart failure, hyperaldosteronism, glaucoma, and diseases caused by retroviruses including HTLV-I, -II, and -III, as well as the use of the peptides as diagnostic tools, and the methods for preparing the peptides.

U.S. Pat. No. 4,725,584 covers 1-peptidyl 1-amino 2,4-diols of formula

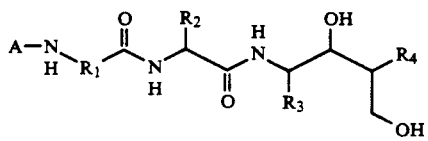

wherein A is an N-protecting group, $R_1$ is arylmethyl, $R_2$ is alkyl of one to six carbons or imidazolyemethyl, $R_3$ is cycloalkylalkyl, and $R_4$ alkyl, alkylmercapto or alkylsulphonyl wherein each alkyl can be from one to six carbons.

European Application Publication No. 202,577 discloses certain N(acyldipeptidyl)-aminoglycols of formula

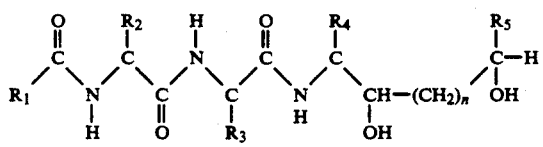

wherein $R_1$ is alkoxy containing one to six carbon atoms or lower alkyl containing one to six carbon atoms; $R_2$ is benzyl or napthylmethyl, $R_3$ is lower alkyl containing one to six carbon atoms or imidazolemethyl; $R_4$ is benzyl, $R_5$ is hydrogen or lower alkyl and n is 0 or 1.

R. Metternich and W. Liidi, Tet. Lett 29, 3923–6 (1988) discloses an aldol approach starting directly from a pyruvate enol and reacting it chelate-controlled with the chiral α-aminoaldehyde thus obtaining the aldol adduct and converting this by 1,3-induced asymmetric hydrogenation into chiral γ-(aminoalkyl)-α-hydroxy-γ lactones which are used in the synthesis of renin inhibitors.

Structurally the positions of the various amino acids of the compounds of the instant invention may be designated by reference to the octapeptide which is the minimal angiotensinogen sequence cleaved by renin, namely:

$$His^6-Pro^7-Phe^8-His^9-Leu^{10}-Val^{11}-Val^{12}-Tyr^{13}$$

↑
scissile bond $$P_5-P_4-P_3-P_2-P_1-P_1{'}-P_2{'}-P_3{'}$$

A designation for the compounds of this invention is illustrated below. The diaminodiol is considered to occupy the $P_1$-$P_2{'}$ positions. For example

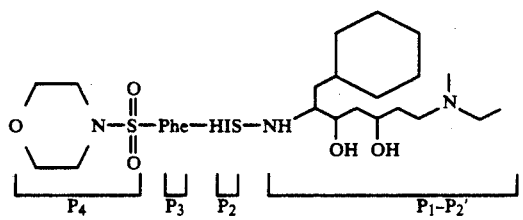

SUMMARY OF THE INVENTION

The present invention relates to novel peptides of the formula $$A\text{-}X\text{-}Y\text{-}W \qquad (I)$$

and the pharmaceutically acceptable acid addition salts thereof wherein A, X, Y, W are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a peptide of formula I in admixture with a pharmaceutically acceptable carrier or excipient, and a method for treating congestive heart failure in a patient suffering therefrom comprising administering to said patient the above pharmaceutical composition in unit dosage form.

The invention also includes a pharmaceutical composition comprising an amount of a peptide of formula I effective for treating diseases caused by retroviruses including HTLV-I, II, and III in admixture with a pharmaceutically acceptable carrier or excipient. A method for treating said diseases in a patient suffering therefrom by administering the above composition in unit dosage form is also included.

The invention also includes a pharmaceutical composition comprising an amount of a peptide of formula I, effective for treating glaucoma in admixture with a pharmaceutically acceptable carrier or excipient. A method for treating glaucoma is also included.

The present invention also includes the use of peptides of formula I above as diagnostic tools for the identification of cases of hypertension due to renin excess.

The invention further includes methods for preparing peptides of formula I above.

The invention further includes novel intermediates useful in the preparation of compounds of the invention.

DETAILED DESCRIPTION

The following table provides a dictionary of the terms used in the description of the invention.

TABLE I

| Abbreviated Designation | |
|---|---|
| | Amino Acid |
| Ala | L-Alanine |
| Phe | L-Phenylalanine |
| HOMOPHE | S-2-Amino-4-phenylbutyric acid |
| Lys | L-Lysine |
| NAPHTHYLALA | 1-Naphthylalanine |
| CYCLOHEXYLALA | Cyclohexylalanine |
| Tyr(OMe) | O-Methyl-L-tyrosine |
| Tyr | L-Tyrosine |
| TZA | S-2-Amino-3-(4-thiazolyl) propionic acid (Thiazolylalanine) |
| His | L-Histidine |
| Gly | Glycine |
| Leu | L-Leucine |
| Met | L-Methionine |
| Alg | S-2-Amino-4-pentenoic acid (allyl glycine) |
| PPG | S-2-Amino-4-pentynoic acid (propargyl glycine) |
| PGY | S-2-Amino-pentanoic acid (propyl glycine) |
| BGY | S-2-Amino-hexanoic acid (butyl glycine) |
| NIA | S-2-Amino-3-cyanopropanoic acid (nitrile alanine) |
| Z | Benzyloxycarbonyl |
| BOC | Tert-butyloxycarbonyl |
| TR | Triphenylmethyl |
| | Acyls |
| IVA | Isovaleryl |
| BNMA | Bis-(1-naphthylmethyl)-acetyl |
| | Esters With |
| —OCH$_3$ | Methanol |
| —OC$_2$H$_5$ | Ethanol |
| —OCH(CH$_3$)$_2$ | 2-Propanol |
| —OC(CH$_3$)$_3$ | tert-Butanol |
| | Solvents and Reagents |
| CHCl$_3$ | Chloroform |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| Et$_3$N | Triethylamine |
| THF | Tetrahydrofuran |
| CH$_2$Cl$_2$ | Dichloromethane |
| MeOH | Methanol |
| EtOAc | Ethyl acetate |

The peptides of the present invention are represented by the formula

or a pharmaceutically acceptable acid addition salt thereof, wherein
A is BOC, IVA, BMA,

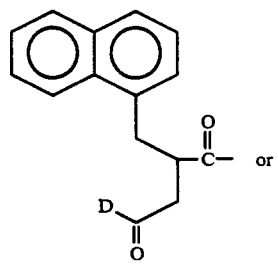

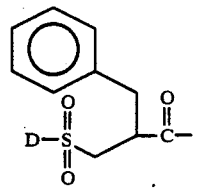

wherein:
R,R$^1$ are each independently H, CH$_3$, C$_2$H$_5$, n-C$_3$H$_7$ or i-C$_3$H$_7$

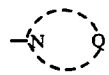

is a saturated ring containing two to five carbon atoms with Q=O, S, N-BOC, N-Z, NR or CH$_2$ -D is

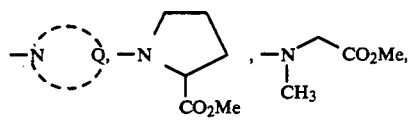

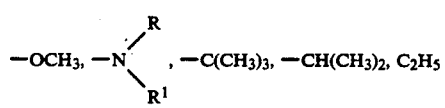

or CH$_3$;
X is absent, Phe, HOMOPHE, NAPHTHYLALA, CYCLOHEXYLALA, Tyr or Tyr(OMe) with the proviso that when A=

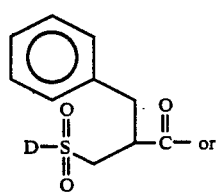

-continued

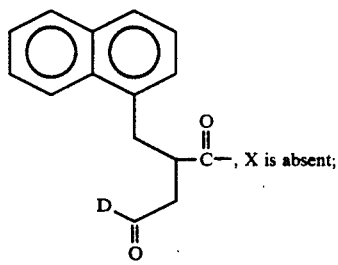, X is absent;

Y is Leu, Ala, Gly PGY, PPG, BGY, Met, His, TZA, Alg, NIA

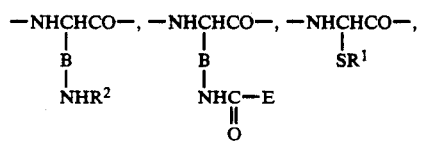

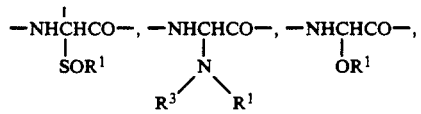

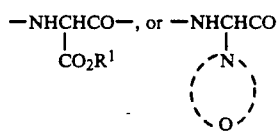

wherein:
(R¹ is as defined above
R² is

E is 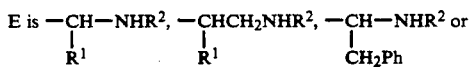

—CHCH₂NHR²;
|
CH₂Ph

B a straight chain of from two to six carbons that is saturated, olefinic or acetylenic.
R³=R¹ and R².

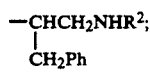

is as defined above;
W is

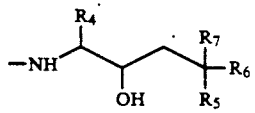

wherein:
R⁴=—CH₂CH(CH₃)₂, —CH₂Ph, —CH₂-cHexyl, —CH₂-cPentyl, or -cHexyl;
R⁵=

OH, OCH₃, OEt, O$\overset{O}{\overset{\|}{C}}$CH₃, O$\overset{O}{\overset{\|}{C}}$NH₂, or OCNHCH₃
$\overset{\|}{O}$ or R⁵ is a keto group with the proviso that either R⁶ or R⁷ is absent.
R⁶, R⁷ are each independently —H, —CH₃, —C₂H₃, —C₂H₅, —C=CH₂, -nC₃H₇,
|
CH³

-iC₃H₇, -nC₄H₉, iC₄H₉, —Ph, -cHexyl, -cPentyl,

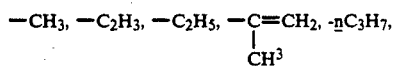, —CH₂CH₂SR,

—CH₂CH₂S(O)R, —CH₂CH₂S(O₂)R, —CH₂Ph,

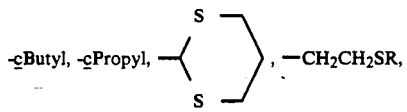

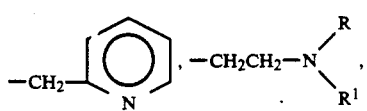

—CH₂OH, —CHO, —CO₂H, —CO₂R,

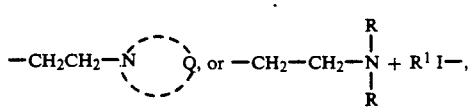

wherein R, R¹ and

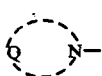

are as defined above.
Preferred compounds of the present invention are those of formula I wherein A is 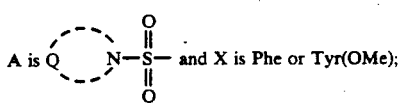 and X is Phe or Tyr(OMe);

Y is His, TZA, NIA, Alg, Lys(CSNHMe) or

-continued
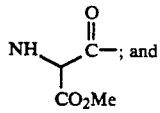
W is
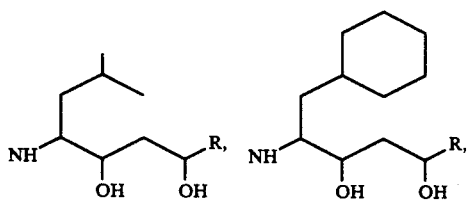
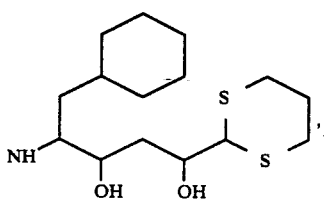
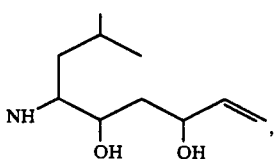
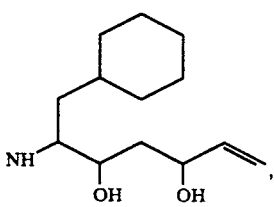
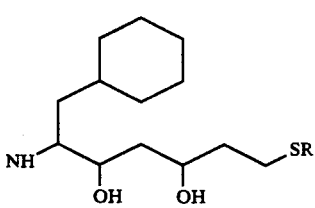
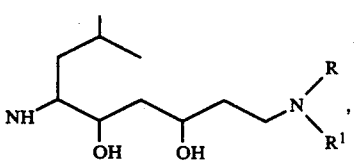
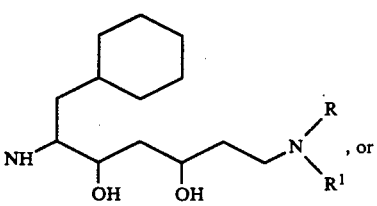
-continued
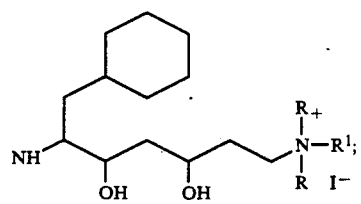
R and $R^1$ are each independently H, $CH_3$, $C_2H_5$, n-$C_3H_7$ or i-$C_3H_7$;
is a saturated ring containing two to five carbon atoms and Q is O, S, NR or $CH_2$ with R defined above.
More preferred compounds of the present invention are those of formula I wherein
A—X is 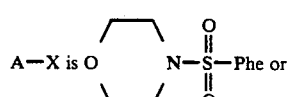 or
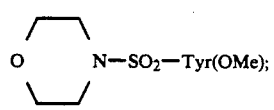
Y is His, TZA, NIA, Alg, Lys(CSNHMe) or
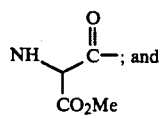
W is
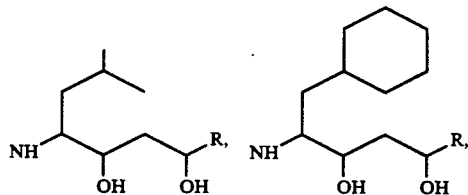
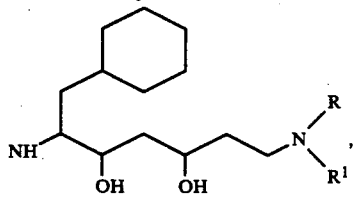
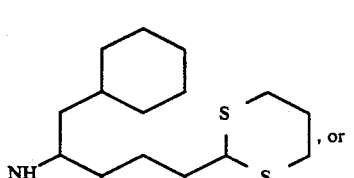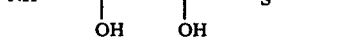

-continued
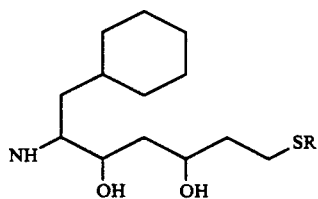
wherein R and R[1] are each independently $CH_3$, $C_2H_5$, $n-C_3H_7$ or $i-C_3H_7$.
Particularly preferred compounds falling within the scope of the invention include the following compounds, their isomers, and pharmaceutically acceptable acid addition salts:
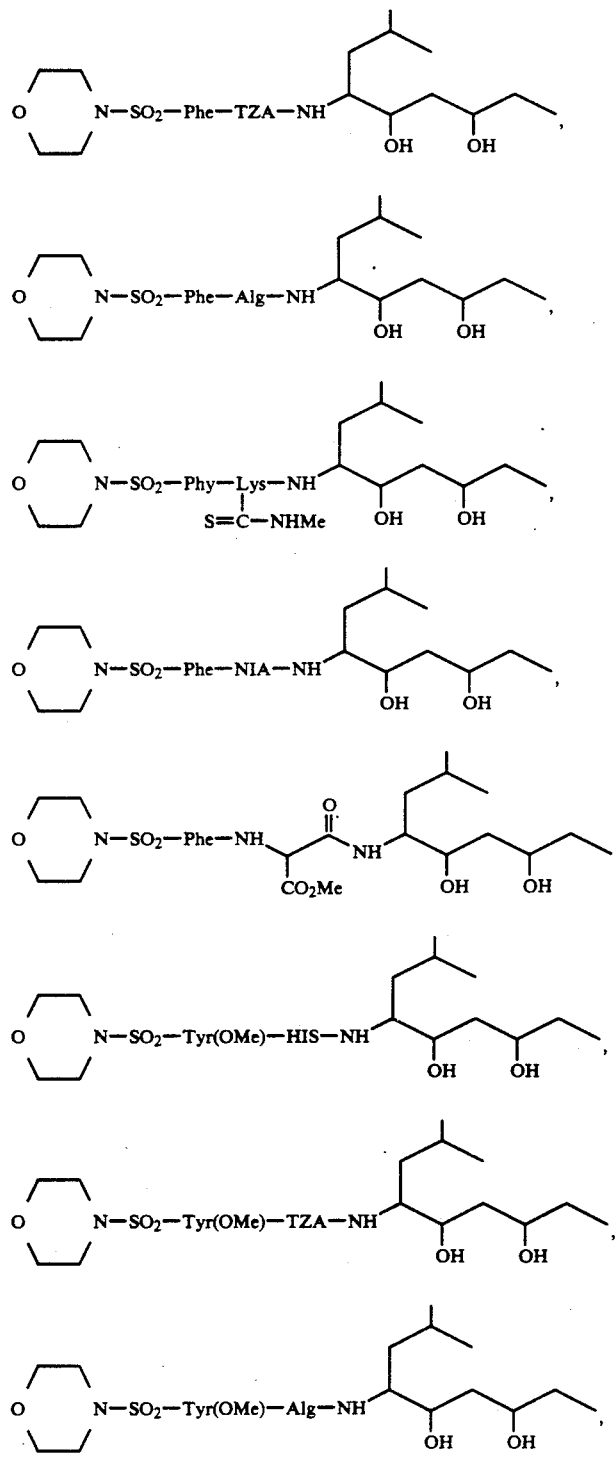

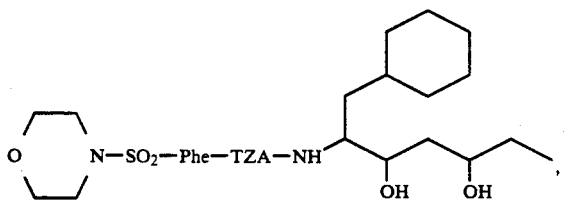
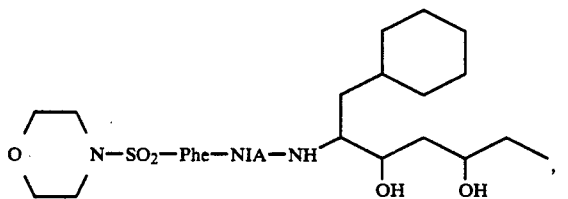
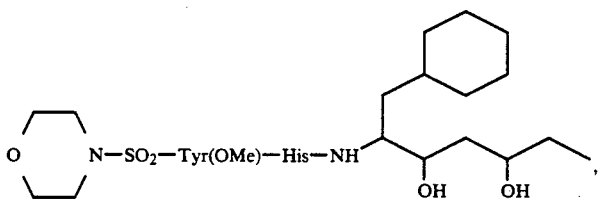
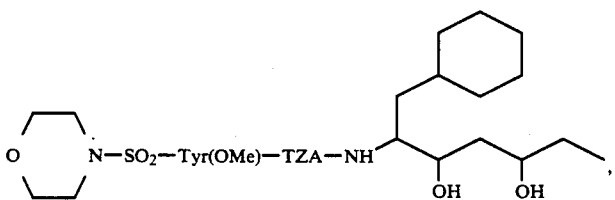
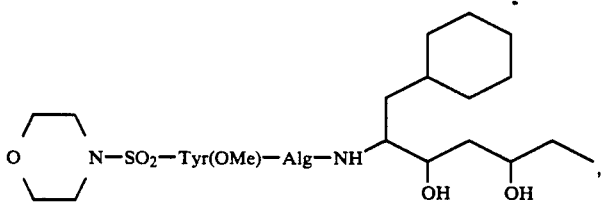
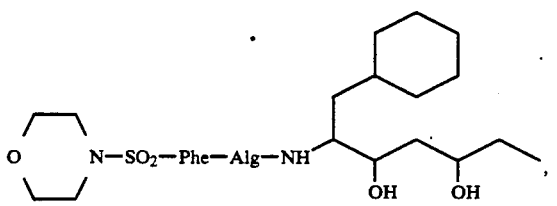
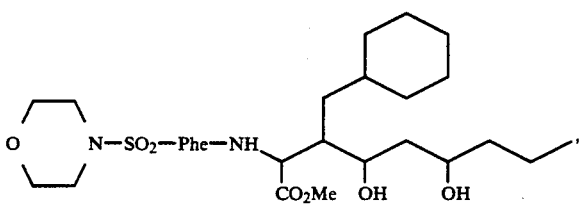

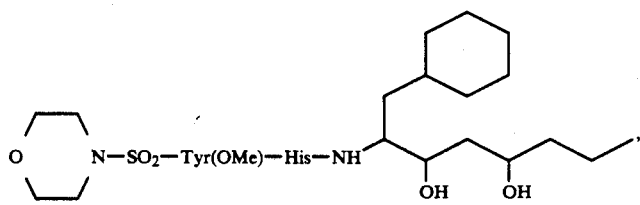
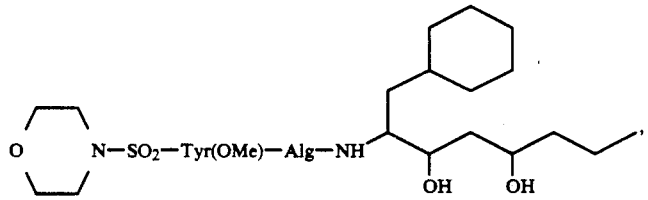
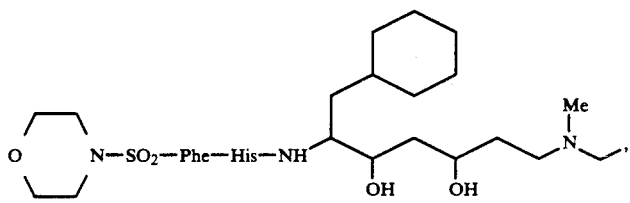
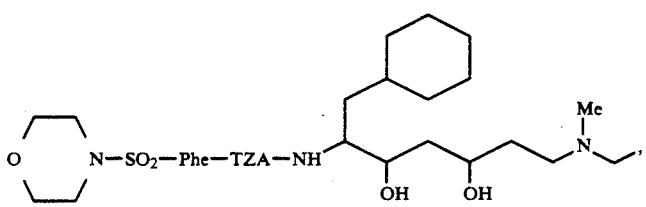
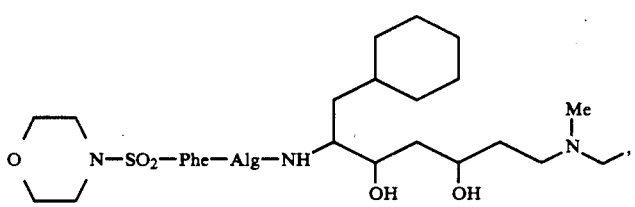
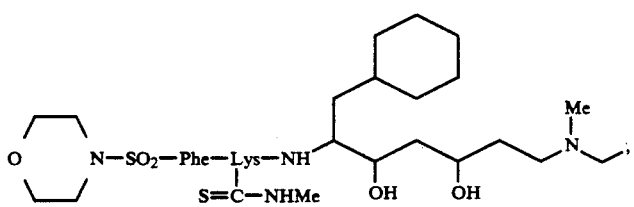
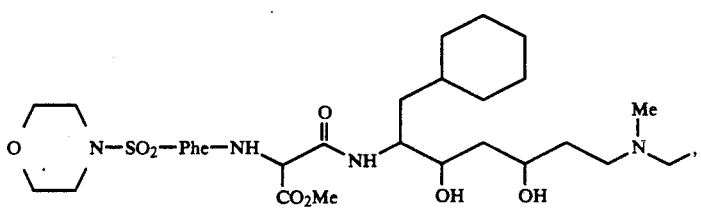

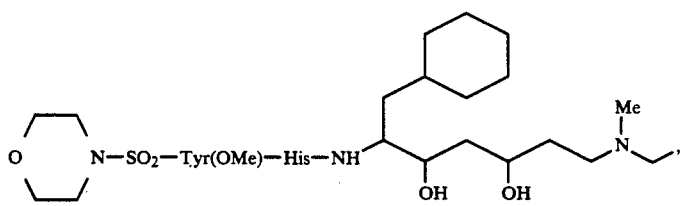
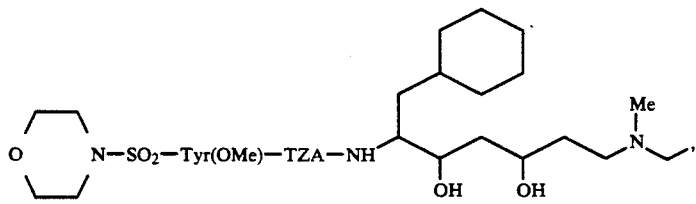
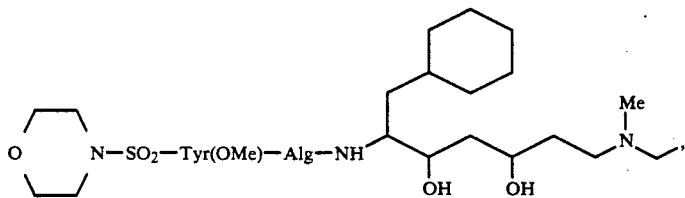
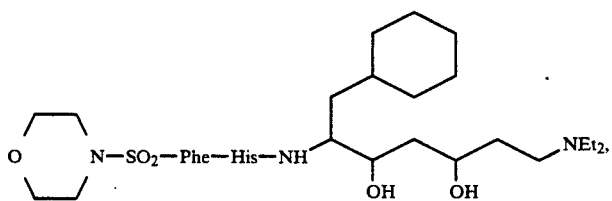
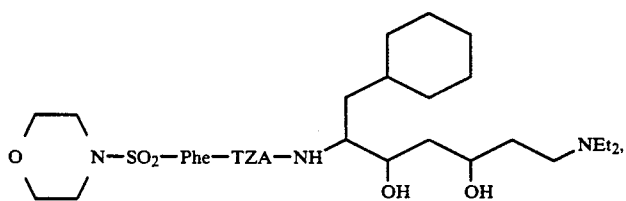
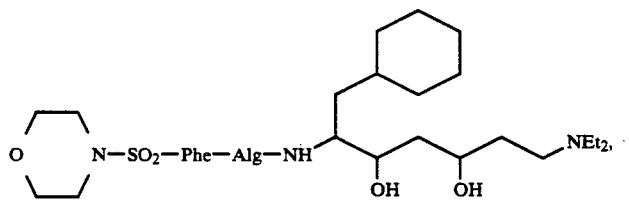
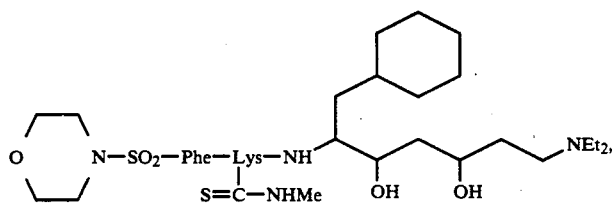

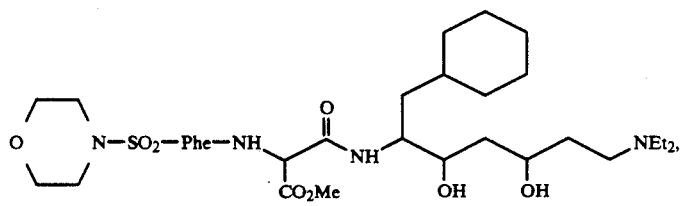
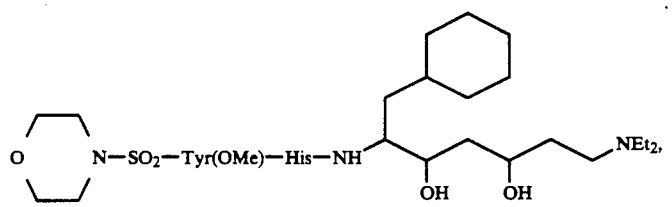
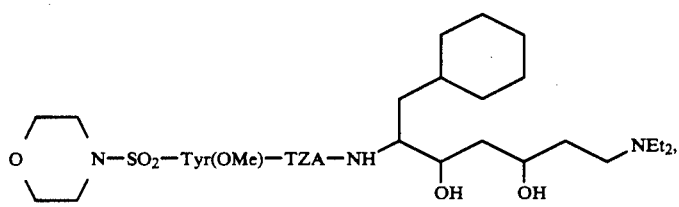
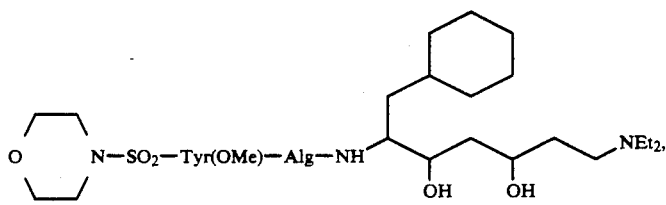
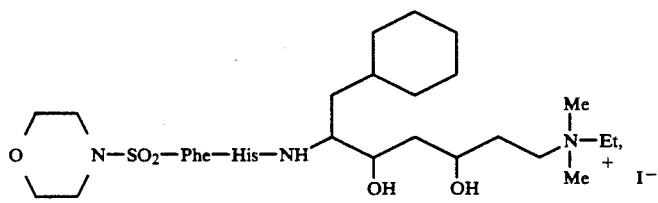
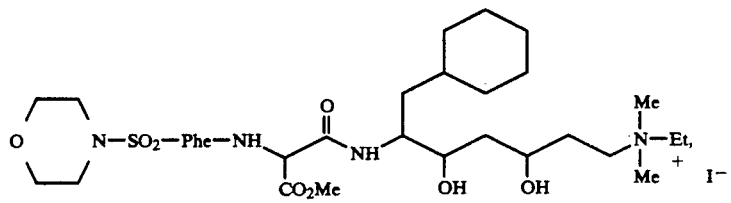
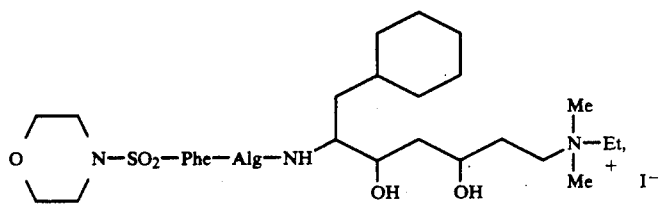

-continued
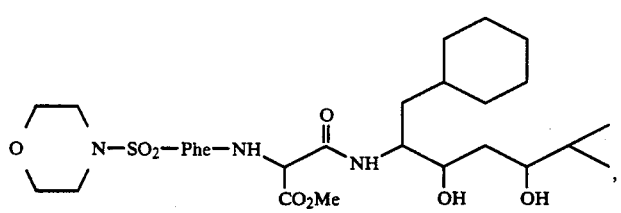
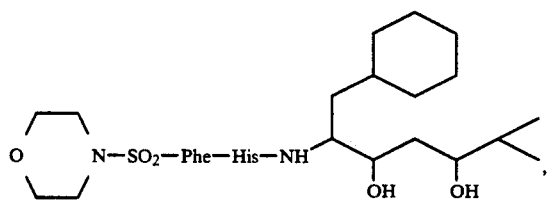
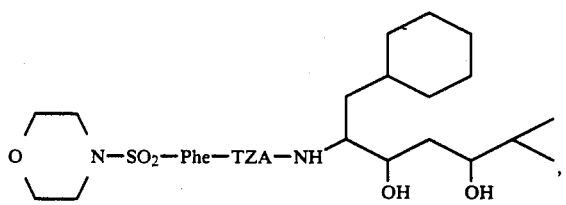
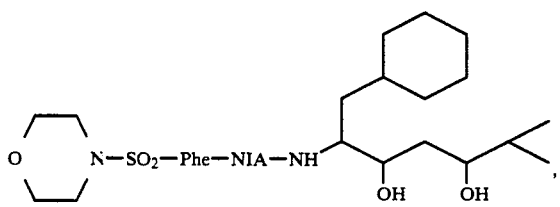
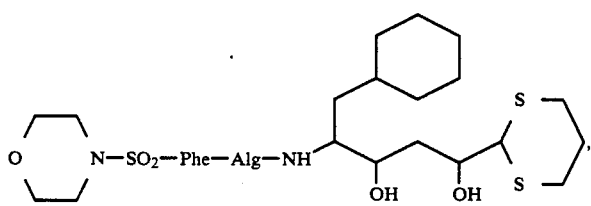
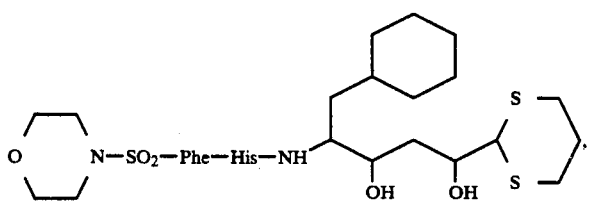
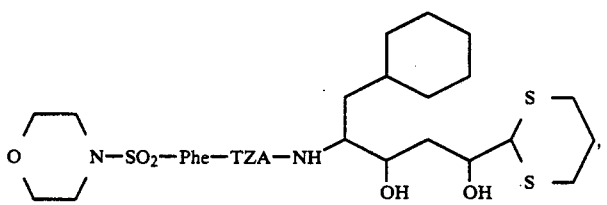

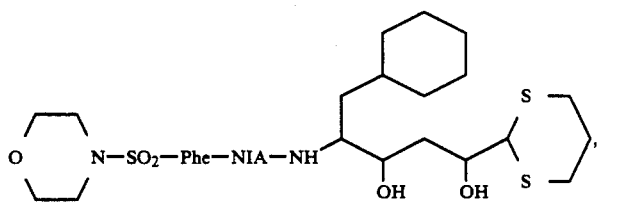
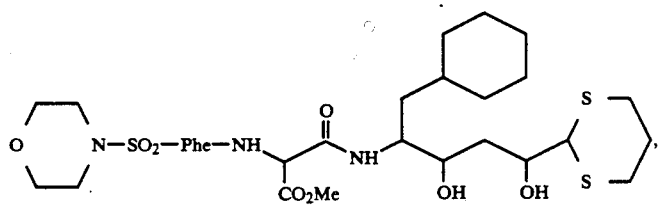
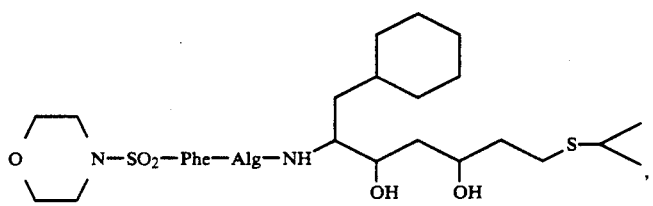
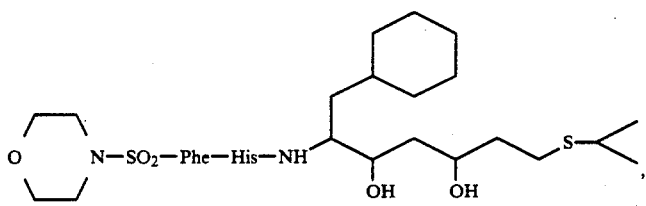
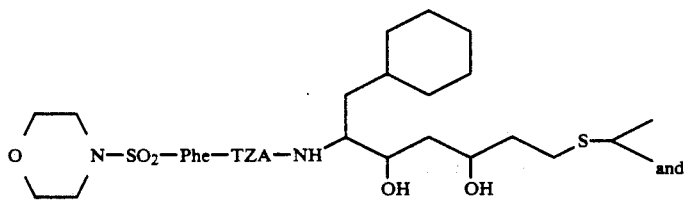
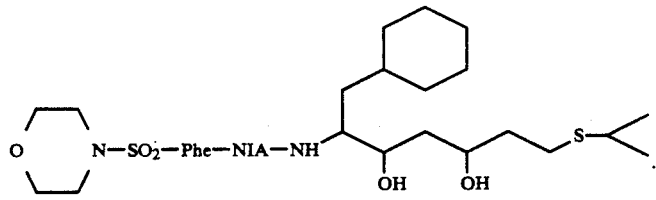
Most preferred compounds are:
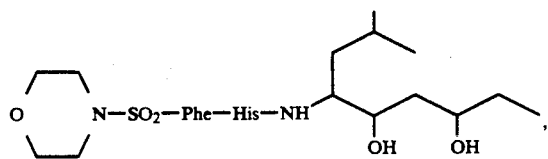

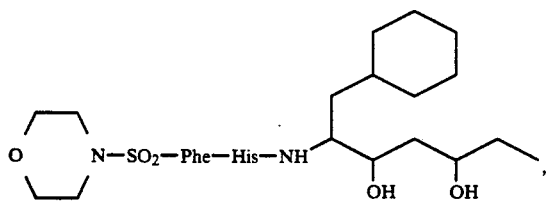
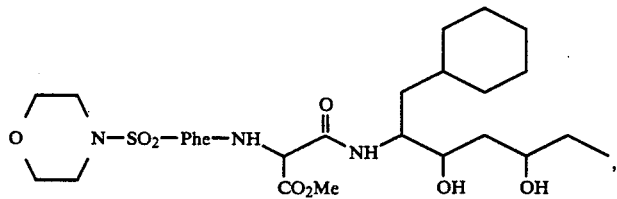
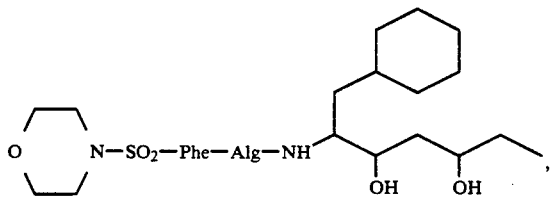
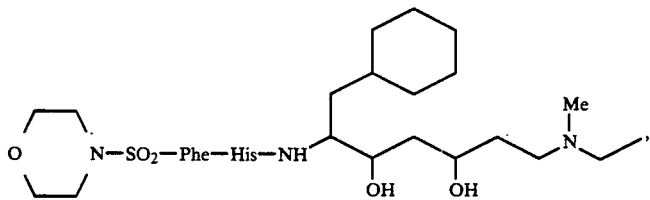
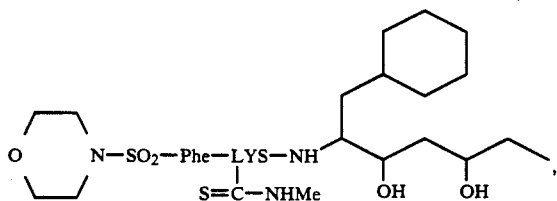
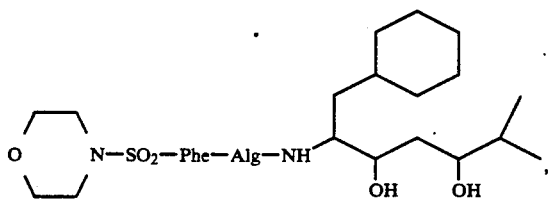
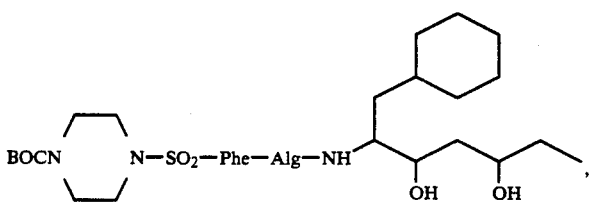

-continued

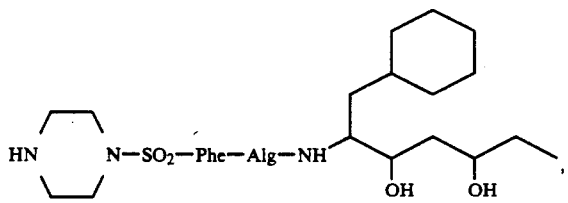

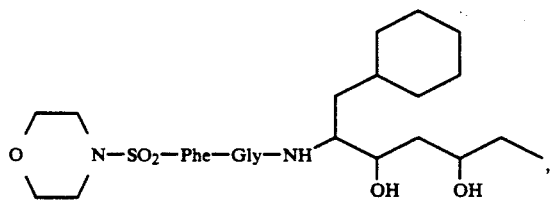

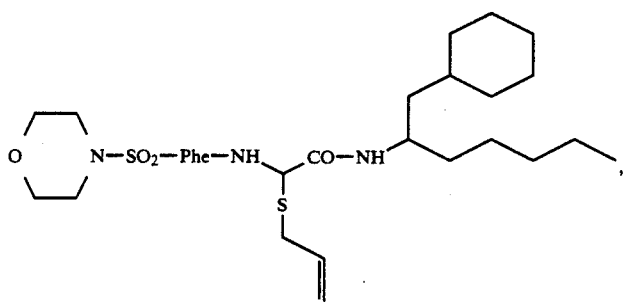

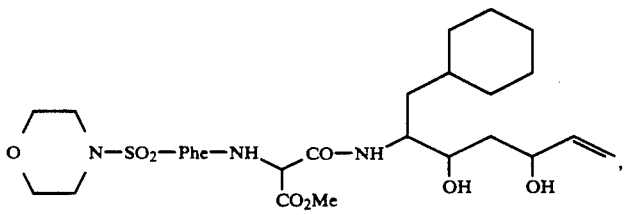

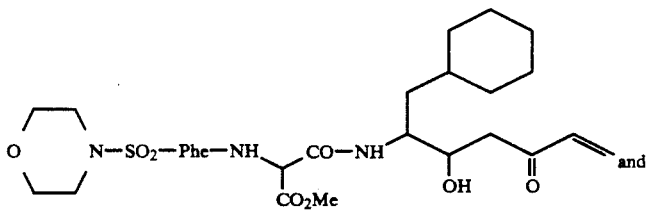

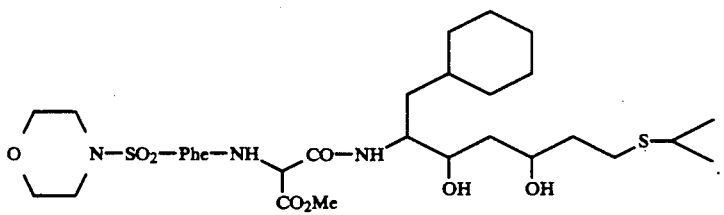

The compounds of the present invention have the advantage of increased hydrophilicity. This property makes the compounds more readily absorbed.

The compounds include solvates and hydrates and pharmaceutically acceptable acid addition salts of the basic compounds of formula I above.

Certain novel intermediates are useful in the preparation of the compounds of the instant invention. They include but are not limited to:

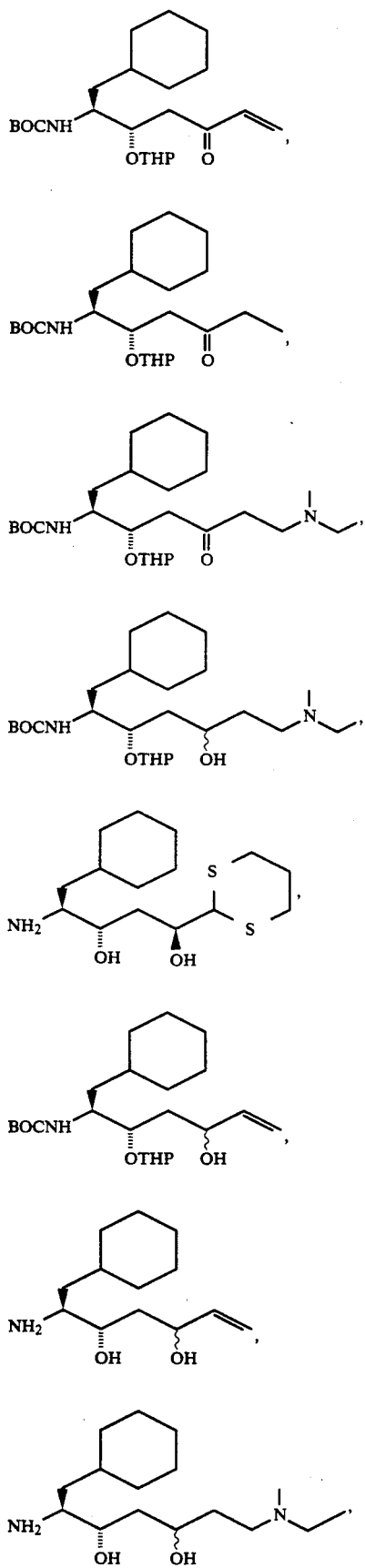
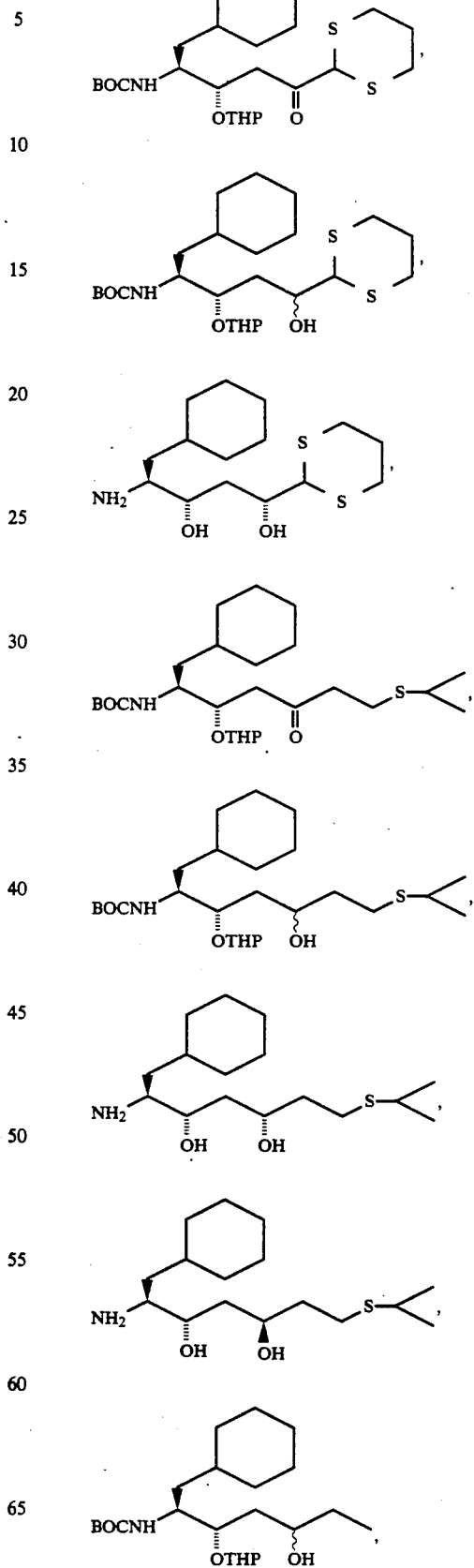

-continued

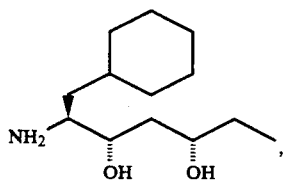

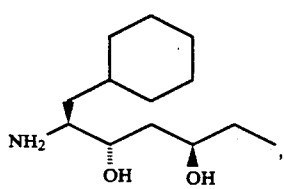

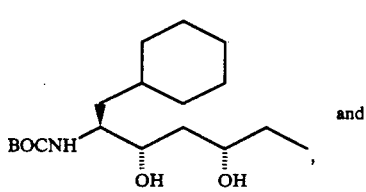 and

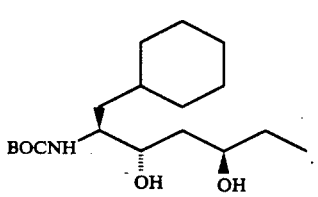

Compounds of formula I may be prepared by a process which comprises:
(a) condensing

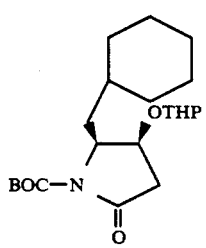

with excess organometallic reagent in an inert solvent to produce

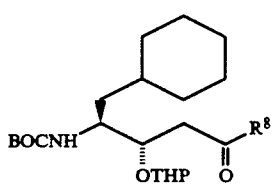

wherein $R^8$ is ethyl, vinyl, isopropyl or 1,3-dithian-2-yl;

(b) reducing with $KBH_4$ the product of step (a) above to produce

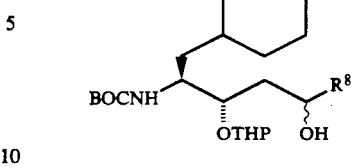

wherein $R^8$ is $C_2H_5$, $C_2H_3$, $CH(CH_3)_2$,

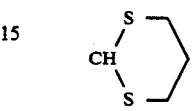

(c) modifying the product of step (a) above wherein $R^8$ is vinyl by reacting with amines or mercaptans to produce

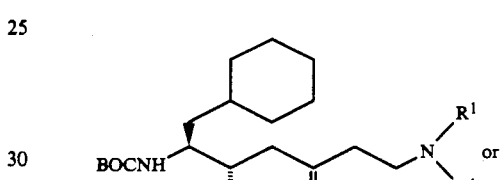

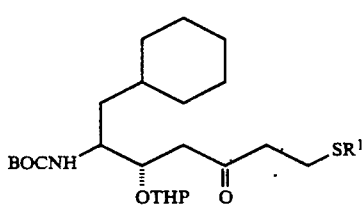

wherein $R^1$ is lower alkyl and then reducing the product with $KBH_4$ to produce

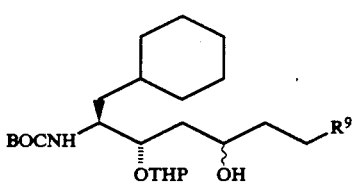

wherein $R^9$ is $N(R^1)_2$ or $SR^1$ (d) reacting

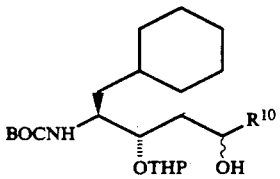

from step (b) or (c) above with

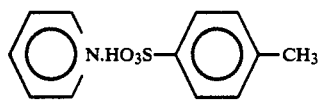

in a protic solvent to produce

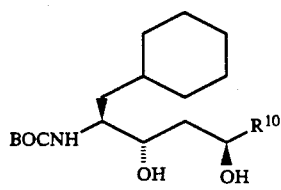

wherein $R^{10}$ is ethyl, vinyl, isopropyl, 1,3-dithian-2-yl,

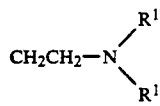

or $CH_2CH_2SR^1$ which are then separated by column chromatography; or (e) alternatively reacting

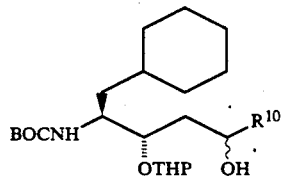

from step (b) or (c) above with methanolic hydrogen chloride in dichloromethane to produce

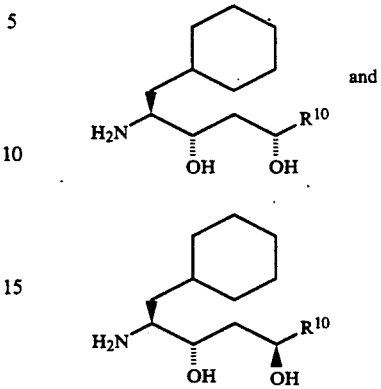

wherein $R^{10}$ is as defined above which are separated by column chromatography; and (f) using the products of step (d) above to produce by known means the desired compound of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in either the R or S configuration. The present invention includes all enantiomeric and epimeric forms as well as the appropriate mixtures thereof. Additionally, the preferred absolute configuration is shown on two illustrative examples below:

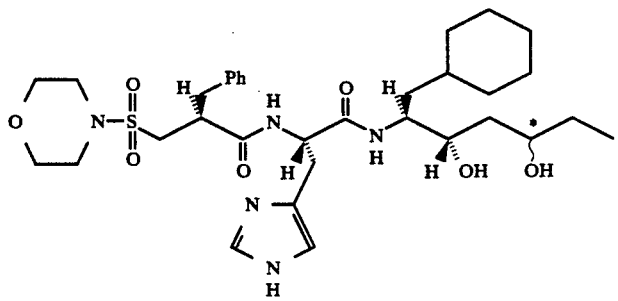

and

-continued

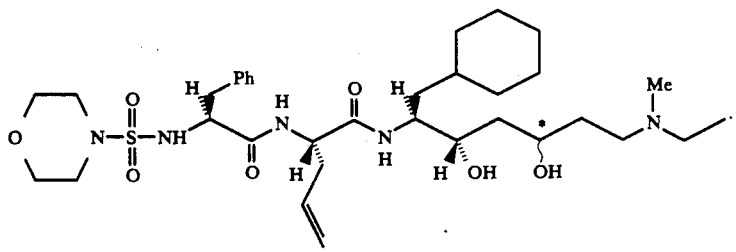

The stereocenter marked with an asterisk is preferred in both R and S configurations as both show renin inhibitory action.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following scheme illustrates novel methods of preparing certain peptides of the present invention.

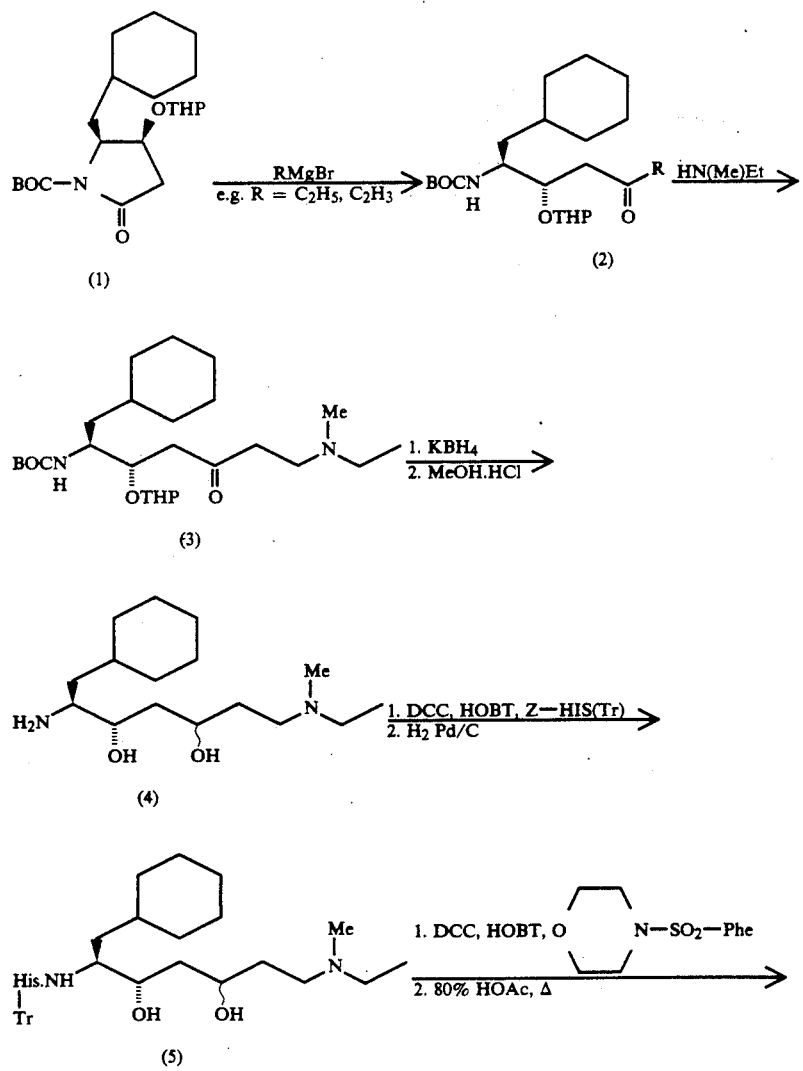

Scheme I
-continued

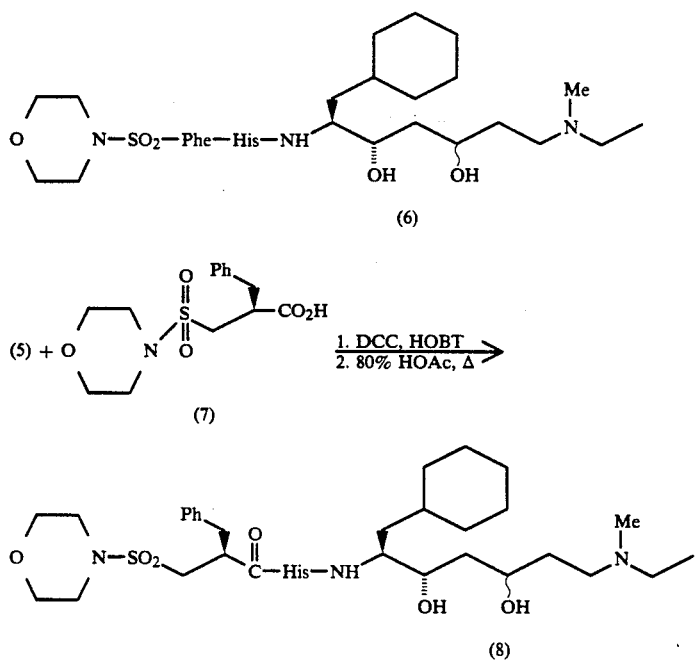

According to Scheme I above, the BOC-lactam, (1) (prepared according to methods found in U.S. Pat. No. 4,876,343 is reacted with excess Grignard reagent such as vinyl or ethyl magnesium bromide in an inert solvent such as ether or THF to afford the ring opened product, (2). In the case of the vinyl adduct the R-side chain may be further modified by Michael additions with amines and mercaptans. Scheme I shows the addition of N-methyl-aminoethane to give (3). Reduction with a hydride agent such as NaBH$_4$, KBH$_4$, ZnBH$_4$, LiBH$_4$ and the like in a protic solvent, such as MeOH, EtOH, iPrOH, H$_2$O, followed by removal of protecting groups with acidic reagents such as MeOH.HCl or TFA affords the aminodiol, (4) as a mixture of two diastereomers that are separated by flash chromatography.

Stepwise coupling and deprotection of Z-His(Tr) and (prepared according to EPA 314060 by methods which are standard to the art of peptide chemistry affords the renin inhibitor, (6). Alternatively, intermediate (5) may be coupled to the carboxylic acid (7) to give the renin inhibitor, (8) after removal of protecting groups. Both diastereomers of intermediate (4) lead to active renin inhibitors. An alternative, highly convergent strategy for synthesis of compounds of the present invention is shown in Scheme II. Selective removal of the THP protecting group from 12, using a mildly acidic reagent such as pyridinium p-toluenesulfonate in a protic solvent such as ethanol, methanol or isopropanol at 20°–70° C. gives the diastereomeric 1,3-diols, 13 and 14. These diols are readily separated by flash chromatography on silica gel. Compounds 13 and 14 are then individually coupled to an A-X-Y fragment such as 15 to afford the desired renin inhibitors, 16 and 17. The A-X-Y fragments are prepared by methods standard to the art of peptide chemistry.

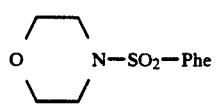

Scheme II

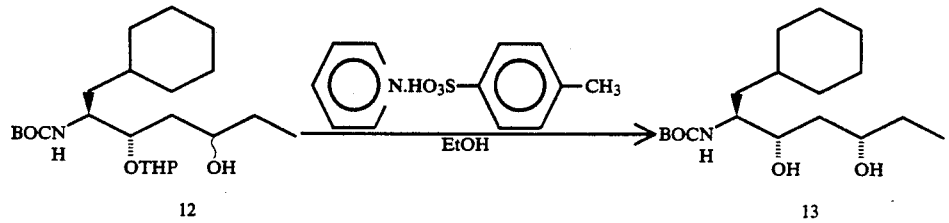

+

-continued
Scheme II

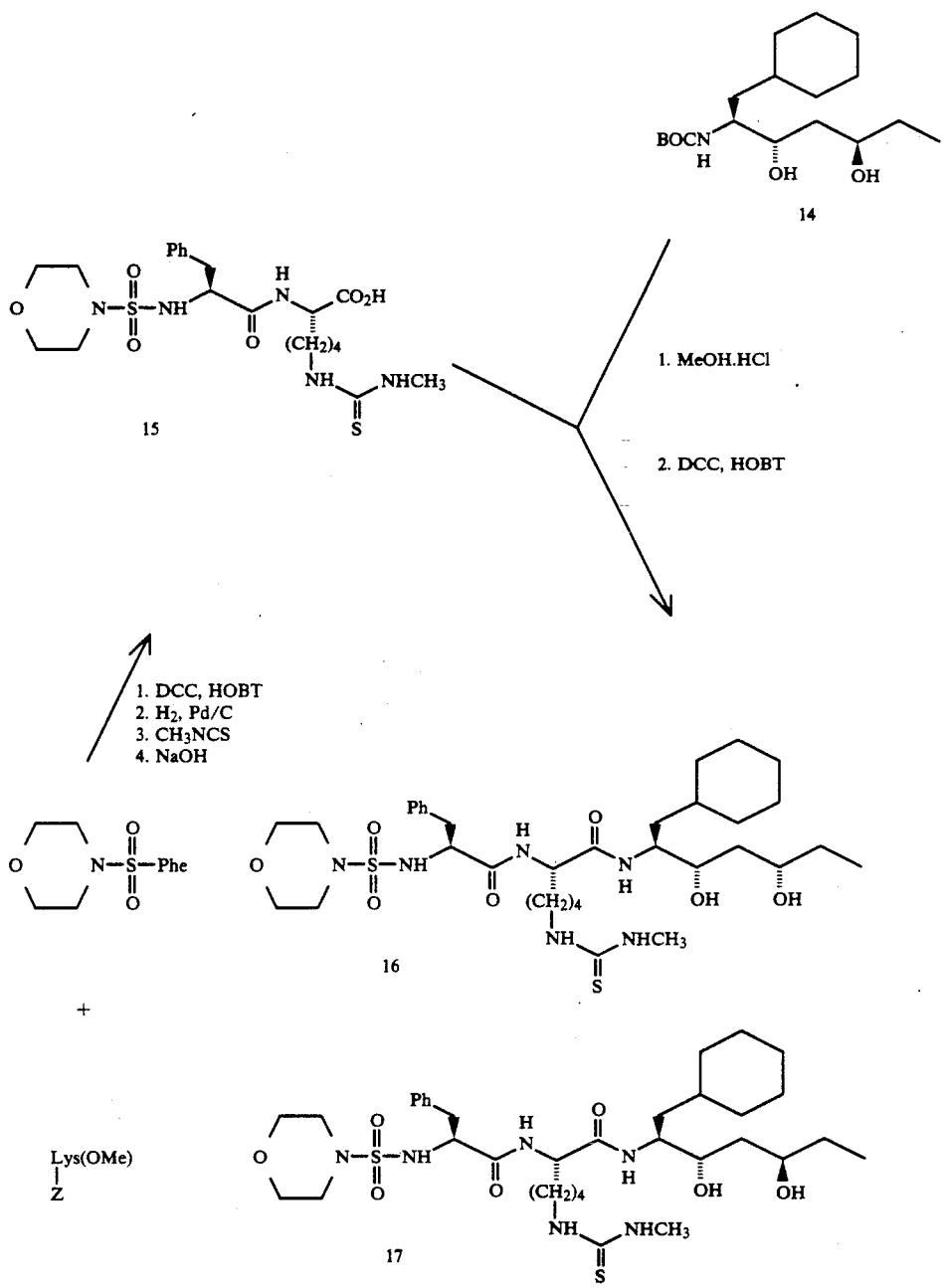

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, N.Y., 1979, Vol. 1, pp. 42–44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, N.Y., 1979, Vol. 1, pp. 241–261.

Peptide coupling depends on activating the carboxy terminus of the amino protected amino acid and condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The term lower alkyl refers to straight or branched chain alkyl radicals containing from one to six carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

Aryl means phenyl, naphthyl or other aromatic groups, including mono- or bicyclic, which may be substituted, especially monosubstituted, by F, Cl, Br, I, $CF_3$, OH, OR, or R, wherein R is lower alkyl.

Heteroaryl means aromatic heterocyclic rings containing at least one heteroatom selected from O, S, and N and from three to five carbon atoms including but not limited to thiazoles and imidazoles.

Aralkyl is as described above for alkyl and aryl, including but not limited to benzyl.

The compounds of the present invention are useful for treating renin-associated hypertension, congestive heart failure, and hyperaldosteronism. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

TABLE II

| Compound | | $IC_{50}$ (nM) |
|---|---|---|
| 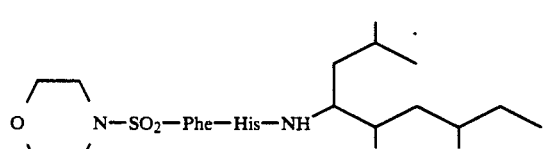 | | 18 |
| 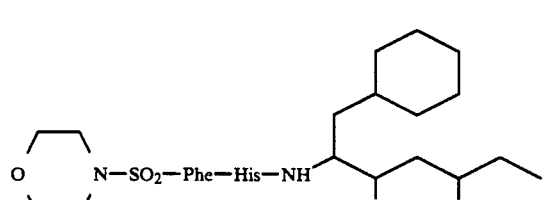 | (Fast isomer)<br>(Slow isomer) | 11<br>1.1 |
| 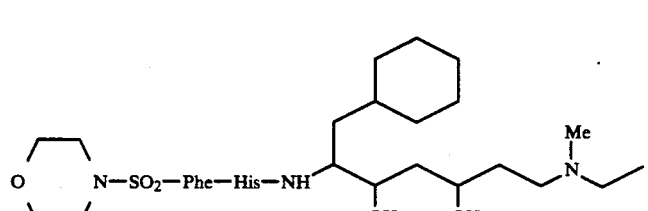 | (Fast isomer)<br>(Slow isomer) | 280<br>220 |
| 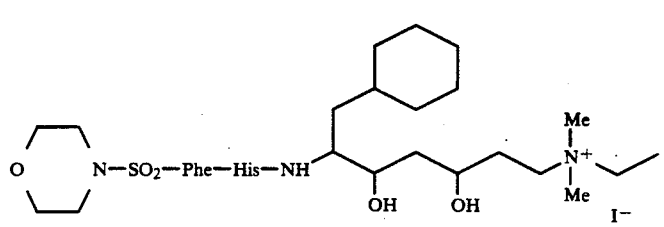 | | 500 |

TABLE II-continued

| Compound | IC$_{50}$ (nM) | |
|---|---|---|
| O(CH$_2$CH$_2$)$_2$N—SO$_2$—Phe—Alg—NH—CH(CH$_2$-cyclohexyl)—CH(OH)—CH$_2$—CH(OH)—CH$_2$CH$_3$ | (Fast isomer) (Slow isomer) | 0.90 0.24 |
| O(CH$_2$CH$_2$)$_2$N—SO$_2$—Phe—Alg—NH—CH(CH$_2$-cyclohexyl)—CH(OH)—CH$_2$—CH(OH)—C(CH$_3$)$_3$ | (Slow isomer) | 0.26 |
| BOC—N(piperazine)N—SO$_2$—Phe—Alg—NH—CH(CH$_2$-cyclohexyl)—CH(OH)—CH$_2$—CH(OH)—CH$_2$CH$_3$ | (Slow isomer) | 0.47 |
| HN(piperazine)N—SO$_2$—Phe—Alg—NH—CH(CH$_2$-cyclohexyl)—CH(OH)—CH$_2$—CH(OH)—CH$_2$CH$_3$ | (Slow isomer) | 1.35 |
| O(CH$_2$CH$_2$)$_2$N—SO$_2$—Phe—Gly—NH—CH(CH$_2$-cyclohexyl)—CH(OH)—CH$_2$—CH(OH)—CH$_2$CH$_3$ | (Fast isomer) (Slow isomer) | >100 43.8 |
| O(CH$_2$CH$_2$)$_2$N—SO$_2$—Phe—Lys(S=CNHCH$_3$)—NH—CH(CH$_2$-cyclohexyl)—CH(OH)—CH$_2$—CH(OH)—CH$_2$CH$_3$ | (Slow isomer) | >100 |
| O(CH$_2$CH$_2$)$_2$N—SO$_2$—Phe—NH—CH(S-allyl)—C(O)—NH—CH(CH$_2$-cyclohexyl)—CH(OH)—CH$_2$—CH(OH)—CH$_2$CH$_3$ | (Fast isomer) | 13.0 |

TABLE II-continued

| Compound | | IC$_{50}$ (nM) |
|---|---|---|
| 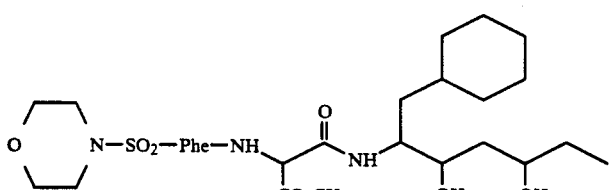 | (Fast isomer)<br>(Slow isomer) | 5.8<br>0.75 |
| 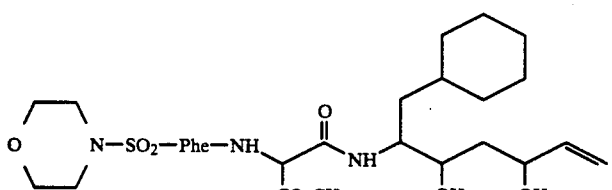 | (Slow isomer) | 2.1 |
| 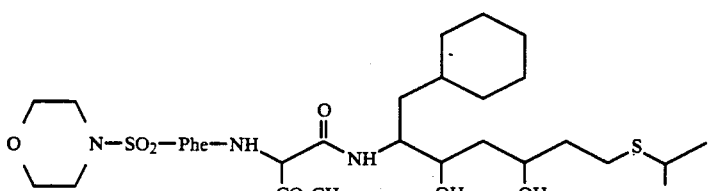 | (Fast isomer)<br>(Slow isomer) | 17.0<br>4.95 |
| 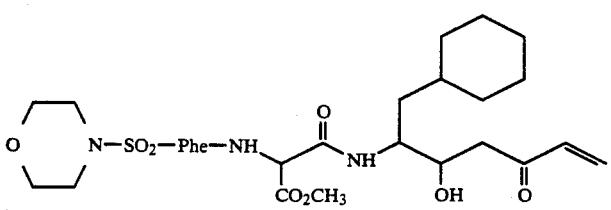 | | 36.4 |

As can be seen from the above table, the compounds of the present invention have a significant effect on the activity of renin and thus are useful for the treatment of hypertension, hyperaldosteronism, and congestive heart failure.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form. the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg/kg of body weight per day or preferably 5 to 750 mg/kg of body weight per day optionally in divided portions. The dosages, however, per day may be varied depending upon the requirements of the patient, the severity of the condition being treated and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

EXAMPLE 1

[1-(Cyclohexylmethyl)-4-oxo-2-[(tetrahydro-2H-pyran-2-yl)oxy]hexyl]carbamic acid, 1,1-dimethylethyl ester (pyran center is RS; other centers are S)

A solution of 15.16 g (0.040 mole) of 5-(cyclohexylmethyl)-4-[(tetrahydro-2H-pyran-2-yl)oxy]-2-oxo-1-pyrrolidinecarboxylic acid, 1,1-dimethylethyl ester, mixture of [4S-[4R*(R*), 5R*] and [4s-[4R*(S*), 5R*]]isomers, in 200 ml of dry tetrahydrofuran is cooled to 5° C. Under nitrogen and with stirring, 27.5 ml (0.055 mole) of 2M ethylmagnesium bromide in tetrahydrofuran is added over a period of five minutes, preventing the temperature from rising above 12° C. with mild cooling. After stirring at 10° C. for one-half hour, the reaction solution is poured, under nitrogen, into a stirred mixture of 300 g of ice and water. Saturated citric acid (200 ml) and 300 ml of ether are added. The organic layer is washed well with water, dried (magnesium sulfate) and concentrated to give 15.80 g of crude product. Silica gel chromatography eluting with hexane to 2:1 hexane-ethyl acetate gives 9.40 g (57%) of pure product; TLC (silica gel, 2:1 hexane-ethyl acetate) Rf 0.6; FAB-MS, MW=411.

EXAMPLE 2

[1-(Cyclohexylmethyl)-4-hydroxy-2-[(tetrahydro-2H-pyran-2-yl)oxy]hexyl]carbamic acid, 1,1-dimethylethyl ester (pyran and 4-hydroxy centers are RS; other centers are S)

A solution of 9.30 g (0.023 mole) of [1-(cyclohexylmethyl)-4-oxo-2-[(tetrahydro-2H-pyran-2-yl)oxy]hexyl]carbamic acid, 1,1-dimethylethyl ester (pyran center is R,S; other centers are S) in 100 ml of absolute ethanol is treated with 0.85 g (0.023 mole) of sodium borohydride. After one and one-half hours stirring at room temperature, acetone (10 ml) is added with mild cooling. After 15 minutes the solution is concentrated at reduced pressure, water (100 ml) is added and the separated oil is extracted into 200 ml of petroleum ether. The dried (potassium carbonate) ether solution is concentrated to give 7.90 g (83%) of alcohol product; TLC (silica gel, 2:1 hexane-ethyl acetate) double spot Rf 0.4–0.5; FAB-MS, MW=413.

EXAMPLE 3

6-Amino-7-cyclohexyl-3,5-heptanediol (3-hydroxy center is RS, other centers are S)

A solution of 7.80 g (0.019 mole) of the product from Example 2 in 100 ml of methylene chloride and 50 ml of methanol is cooled to 5° C. and saturated with hydrogen chloride gas. The solution is allowed to stand at room temperature for six hours and then concentrated at reduced pressure to remove solvent. The crude hydrochloride salt is purified by silica gel chromatography eluting with chloroform to 20% methanol-chloroform; weight 4.10 g (81%); TLC (silica gel, 2:10 methanol-chloroform) one spot, Rf 0.4.

The purified hydrochloride is converted to the base by dissolution in 50 ml of water, addition of 10% potassium carbonate and extraction into 150 ml of ether; MS, MW=229.

EXAMPLE 4

N-[1-(Cyclohexylmethyl)-2,4-dihydroxyhexyl]-L-[N(α)-(phenylmethloxy)carbonyl-N(τ)-triphenylmethyl] histidinamide (Two diastereomers isolated: 4-hydroxy center is R or S, other centers are S)

A solution of 2.60 g (0.011 mole) of 6-amino-7-cyclohexyl-3,5-heptanediol from Example 3 in 50 ml of methylene chloride is treated successively with 1.68 g (0.011 mole) of 1-hydroxybenztriazole hydrate, 5.85 g (0.011 mole) of Z-(trt)His and 2.27 g (0.011 mole) of dicyclohexylcarbodiimide. After standing at room temperature the dicyclohexylurea is filtered and the filtrate is concentrated to ca 15 ml volume. Ether (100 ml) is added and the solution is washed with 100 ml of 3% sodium bicarbonate and then 50 ml of water. After drying over sodium sulfate the ether solution is concentrated to give 8.20 g of crude product. Purification by silica gel chromatography eluting with chloroform to 5% methanol-chloroform gives a fraction enriched in "fast" moving diastereomer (TLC; silica gel, 1:10 methanolchloroform, major spot Rf 0.7, trace spot Rf 0.6) and a fraction enriched in "slow" moving diastereomer with major spot at Rf 0.6 and a trace of Rf 0.7. Each diastereomer shows FAB-MS, MW=742.4.

EXAMPLE 5

N-[1-(Cyclohexylmethyl)-2,4-dihydroxyhexyl]-L-[N($\tau$)-triphenylmethyl)histidinamide ("Fast") isomer: 4-hydroxy center is R or S; other centers are S)

A solution of 2.30 g (0.0031 mole) of enriched "fast" diastereomer from Example 4 in 30 ml of methanol is reduced at low pressure for eight hours with 100 mg of 20% palladium on carbon and hydrogen. The catalyst is filtered and the methanol solution concentrated at reduced pressure. The crude product is chromatographed with silica gel and elution with chloroform to 5% methanol-chloroform to give 1.60 g of a single spot material, Rf 0.3-0.4 (TLC; silica gel, 1:10 methanol-chloroform); FAB-MS, MW=608.3.

EXAMPLE 6

N-1-(Cyclohexylmethyl)-2,4-dihydroxyhexyl]-L-[N($\tau$)-triphenylmethyl]histidinamide ("Slow") isomer: 4-hydroxy center is either R or S; other centers are S)

The "slow" diastereomer from Example 4 is subjected to catalytic debenzylation and purified as in Example 5 to similarly obtain the "slow" isomer, Rf 0.2-0.4 with a trace of Rf 0.3-0.4; FAB-MS, MW=608.3.

EXAMPLE 7

N-(4-morpholinylsulfonyl)-L-phenylalanyl-N-1-(cyclohexylmethyl)-2,4-dihydroxyhexyl]-L-histidinamide (4-hydroxy center is R or S; others are S) ("Fast" isomer)

A solution of 1.45 g (0.0024 mole) of "fast" isomer from Example 5 in 25 ml of methylene chloride is treated successively with 0.37 g (0.0024 mole) of 1-hydroxybenztriazole hydrate, 0.76 g (0.0024 mole) of morpholineosulfonyl-L-phenalanine and 0.50 g (0.0024 mole) of dicyclohexylcarbodiimide. After standing at room temperature overnight the urea is filtered and the filtrate is concentrated at reduced pressure to remove most of methylene chloride. The residue is taken up into 100 ml of ether and the solution is washed with 50 ml of saturated sodium bicarbonate and 50 ml of water. The dried (sodium sulfate) organic phase is concentrated to give 2.00 g of crude product. Purification by silica gel chromatography eluting with chloroform to 5% methanolchloroform gives the trityl protected product; weight 1.65 g; TLC (silica gel, 1:10 methanol-chloroform) Rf 0.5; FAB-MS, MW=904.4.

A solution of 1.60 g (0.0018 mole) of the above adduct in 16 ml of glacial acetic acid is treated with 4 ml of water. The solution is heated at 95° C. for six minutes. Water (25 ml) is added to precipitate triphenylmethyl alcohol. The mixture is cooled in an ice bath and filtered. The filtrate is concentrated at reduced pressure and 75 ml of saturated sodium bicarbonate and 100 ml of methylene chloride are added. The bottom organic layer is separated, dried over potassium carbonate and concentrated to give 1.00 g of crude product. This material is purified by silica gel chromatography eluting with chloroform to 5% methanol-chloroform to give the desired product; TLC; (silica gel, 2:10 methanol-chloroform) Rf 0.6; FAB-MS, MW=662.3.

EXAMPLE 8

N-(4-morpholinylsulfonyl)-L-phenylalanyl-N-[1-(cyclohexylmethyl)-2,4-dihydroxyhexyl]-L-histidinamide (4-hydroxy center is R or S; others are S) ("Slow" isomer)

The "slow" diastereomer from Example 6 is coupled to morpholinosulfonyl-L-phenylalanine as in Example 7 giving a material moving slower on TLC (silica gel, 1:10 methanol-chloroform) Rf 0.45 with traces at Rf 0.4 and 0.5; FAB-MS, MW=904.4.

This isomer is detritylated as in Example 7 for the "fast" isomer to give "slow" moving product on TLC (silica gel, 2:10 methanol-chloroform) Rf 0.55; FAB-MS, MW=662.3. Note: The slow and fast isomers were compared side by side and mixed on TLC. Also, the NMR showed diastereomeric differences.

EXAMPLE 9

[1-(Cyclohexylmethyl)-4-oxo-2-[tetrahydro-2-H-pyran-2-yl)oxy]-5-hexenyl]carbamic acid, 1,1-dimethylethyl ester (pyran center is RS; other centers are S)

A solution of 51.36 g (0.135 mole) of 5-(cyclohexylmethyl)-4-[(tetrahydro-2H-pyran-2-yl)oxy]-2-oxo-1-pyrrolidinecarboxylic acid, 1,1-dimethylethyl ester, mixture of [4S-[4R*(R*), 5R*] and [4S-[4R*(S*), 5R*]]isomers, in 500 ml of tetrahydrofuran is cooled to 5° C., under nitrogen with stirring. A quantity of 175 ml (0.175 mole) (30% excess) of 1M vinylmagnesium bromide in tetrahydrofuran is added over 20 minutes, keeping the temperature at 5° C. The solution is allowed to warm to 15° C. and maintained there for one-half hour. The solution is poured into 800 ml of ice and water with stirring. Saturated citric acid (300 ml) and ether (800 ml) are added. The aqueous layer is separated. The organic layer is washed well with water, dried (magnesium sulfate) and concentrated; wt 57.0 g. Silica gel chromatography, eluting with hexane and then 2:1 hexane-ethyl acetate gives purified vinyl ketone; TLC (2:1 hexane-ethyl acetate) RF 0.6.

EXAMPLE 10

[1-(Cyclohexylmethyl)-6-(ethylmethylamino)-4-oxo-2-[(tetrahydro-2-H-pyran-2-yl)oxy]hexyl]carbamic acid, 1,1-dimethylethyl ester (pyran center is RS; other centers are S)

A solution of 14.33 g (0.035 mole) of the vinyl ketone from Example 9 in 100 ml of methylene chloride is treated with 4.14 g (0.07 mole) of N-ethylmethylamine. After one hour the solvent and excess amine are evaporated to give product; TLC (2:1 hexane-ethyl acetate, silica gel) RF 0.1; FAB-MS shows MW=468.

EXAMPLE 11

[1-Cyclohexylmethyl)-6-(ethylmethylamino)-4-hydroxy-1,1-dimethylethyl ester (pyran center and 4-hydroxy center are RS; other centers are S)

A quantity of 20 ml of water is added to a solution of 16.40 g (0.035 mole) of the amino ketone in 200 ml of methanol. This solution is treated with a solution of 1.89 g (0.035 mole) of potassium borohydride in 20 ml of water, cooling to keep the temperature at 20° C. After one hour, 20 ml of acetone is added. After 15 minutes the methanol is removed at reduced pressure and the separated gum is extracted into a solution of 300 ml of ether and 50 ml of methylene chloride. The organic phase is dried (potassium carbonate) filtered and evaporated to give product; TLC (2:10 methanol-chloroform, silica gel) RF 0.2–0.4, two overlapping spots); DEI-MS shows MW=470.

EXAMPLE 12

6-Amino-7-cyclohexyl-1-(ethylmethylamino)-3,5-heptanediol (3-hydroxy center is RS, other centers are S)

A solution of 16.0 g (0.034 mole) of the blocked amino alcohol from Example 11 in 100 ml of methylene chloride is diluted with 200 ml methanol and cooled on an ice bath under nitrogen. The cold solution is then charged with a vigorous stream of dry hydrogen chloride for five minutes and subsequently allowed to stand at room temperature overnight. The solvent and excess hydrogen chloride are removed at reduced pressure. The dihydrochloride residue is converted to the base by dissolution is 20 ml of water, charcoaling, filtering, saturating with potassium carbonate and extracting into 300 ml of methylene chloride (top layer). The organic solution is dried (potassium carbonate) and concentrated; wt 11.00 g of mixed diastereomers as a crude oil. Purification is effected by silica gel chromatography as follows: The column is packed with 1:10 methanol-chloroform. The column is further deactivated by passage of two column volumes of 3:10:0.3 methanol-chloroform-conc. ammonium hydroxide and then two column volumes of chloroform. The diamino diol is placed on the column as a chloroform solution and eluted to separate diastereomers with 3:10:0.3 methanol-chloroform-conc. ammonium hydroxide, giving 2.98 g of fast spot material, TLC; Rf 0.4 (3:10:0.3 methanol-chloroform-ammonium hydroxide, silica gel, and 3.69 g of slow spot material, Rf 0.3 (same TLC system); DEI-MS shows MW=286 for both diastereomers.

EXAMPLE 13

N-(4-Morpholinosulfonyl)-L-phenylalanyl-N-[1-(cyclohexylmethyl)-6-(ethylmethylamino)-2,4-dihydroxyhexyl]-L-histidinamide ("Fast" isomer: 4-hydroxy center is R or S, other centers are S)

The diaminodiol "fast" isomer from Example 12 is sequentially coupled to histidine and N-morpholinosulfonyl-L-phenylalanine as described in Examples 5 and 7 lo afford the "fast" isomer of the desired product; TLC (silica gel, chloroform-methanol-conc. NH$_4$OH$_{(aq)}$, 10:3:0.3) R 0.4; FAB-MS shows MW=720.

EXAMPLE 14

N-(4-Morpholinosulfonyl)-L-phenylalanyl-N-[1-(cyclohexylmethyl)-6-(ethylmethylamino)-2,4-dihydroxyhexyl]-L-histidinamide ("Slow" isomer: 4-hydroxy center is R or S, other centers are S)

The diaminodiol "slow" isomer from Example 12 is sequentially coupled to histidine and N-morpholinosulfonyl-L-phenylalanine as described in Examples 5 and 7 to afford the "slow" isomer of the desired product; TLC (silica gel, chloroform-methanol-conc. NH$_4$OH-$_{(aq)}$, 10:3:0.3) Rf 0.3; FAB-MS shows MW=720.

EXAMPLE 15

N-(4-Morpholinosulfonyl)-L-phenylalanyl-N-1-(cyclohexylmethyl)-6-(ethyldimethylammonium)-2,4-dihydroxyhexyl]-L-histidinamide iodide ("Slow" isomer: 4-hydroxy center is R or S, other centers are S)

A solution of 0.33 g (0.00045 mole) of the "slow" isomer of Example 14 in 5 ml of methylene chloride is diluted with 1 ml of ether and cooled to 10° C. A solution of 0.065 g (0.0045 mole) of methyl iodide in 1 ml of methylene chloride is added and the solution is allowed to warm to room temperature. After three days standing the supernatant is decanted from the separated gum and the gum is triturated with 5 ml of methylene chloride. Decantation leaves 0.45 g of product. Purification is effected by dissolution in ca. 2 ml of methanol and precipitation as an amorphous solid with 25 m of ether. Filtration gives 0.49 g of product; HPLC, 92.7%; NMR (δ, DMSO-d$_6$), 2.98 (S, 6H, +N(Me)$_2$).

EXAMPLE 16

N-(4-Morpholinosulfonyl)-L-phenylalanyl-L-[N(ε)-phenylmethyloxycarbonyl)]lysine, methyl ester A mixture of N-(4-morpholinosulfonyl)-Phe (3.15 g, 10 mmol), DCC (2.1 g, 10 mmol), HOBT (1.35 g, 10 mmol) and DMF (20 ml) was stirred at 20° C. for five minutes. The resulting slurry was treated consecutively with N(ε)-Z-Lys(OMe).HCl (3.32 g, 10 mmol), triethylamine (1.4 ml, 10 mmol) and CH$_2$Cl$_2$ (10 ml), The reaction was stirred for 48 hours at 20° C. then CH$_2$Cl$_2$ was evaporated. Ethyl acetate was added and the solids were removed by filtration. Evaporation of the filtrate gives a wet solid that was triturated with water, dissolved in CHCl$_3$ and washed with 5% K$_2$CO$_3$ (aq). The organic layer was dried over MgSO$_4$ and evaporated to a pale yellow solid. Trituration with ethyl acetate gives 5.3 g of a colorless solid. TLC (silica gel, CHCl$_3$-MeOH, 9:1); Rf 0.75.

EXAMPLE 17

N-(4-Morpholinosulfonyl)-L-phenylalanyl-L-[N(ε)-(N-methylthiocarbamyl)]lysine, methyl ester A solution of the product from Example 16 (5.28 g, 8.95 mmol) in THF (125 ml) was treated with 20% Pd/C (0.55 g) under an atmosphere of hydrogen. After three hours, methanol (125 ml) was added and catalyst removed by filtration. The resulting solution was treated with methyl isothiocyanate (0.7 g, 9.6 mmol) and stirred 18 hours at 20° C. Evaporation gave a solid that was recrystallized from hot CHCl$_3$ by dropwise addition of ether to give the desired product (4.25 g); FAB-MS, MW=529.

EXAMPLE 18

N-(4-Morpholinosulfonyl)-L-phenylalanyl-L-[N(ε)-(N-methylthiocarbamyl)]lysine

The product from Example 17 (4.25 g, 8,.02 mmol) was dissolved in THF (50 ml) and 1N NaOH (20 ml) added. The reaction mixture was stirred at ambient temperature for 24 hours and the solution diluted with water (200 ml). The mixture was acidified to pH 2 with 2N HCl and extracted three times with methylene chloride. The combined organic layers were dried over anhydrous magnesium sulfate, filtered, and evaporated to dryness to give 3.98 g; FAB-MS, MW=515.

EXAMPLE 19

[1-(Cyclohexylmethyl)-2,4-dihydroxyhexyl]carbamic acid, 1,1-dimethylethyl ester (Two diastereomers isolated: 4-hydroxy center is either R or S, other centers are S)

To a solution of the product from Example 2 (14.1 g, 34.09 mmol) in absolute ethanol (140 ml) was added pyrridinium-p-toluene-sulfonate (0.86 g, 3.41 mmol). The reaction mixture was heated at 55° C. for three hours and the solvent removed under reduced pressure. The residue was taken up in ethyl acetate and extracted twice with water. The organic layer was dried over anhydrous magnesium sulfate, filtered, and the filtrate evaporated under reduced pressure to give 13.74 g of a mixture of diastereomers. The diastereomers were separated by flash chromatography eluting with a solvent gradient of 5 to 40% ethyl acetate in hexane to give 5.72 g (51% yield) of the fast isomer and 4.72 g (42% yield) of the slow isomer; CI-MS shows MW=329 for both diastereomers.

EXAMPLE 20

6-Amino-7-cyclohexyl-3,5-heptane diol hydrochloride ("Slow" isomer: 3-hydroxy center is either R or S, other centers are S, one of two diastereomers found in Example 3)

The slow isomer from Example 19 (2.25 g, 6.83 mmol) was dissolved in methylene chloride (25 ml) and MeOH/HCl (0.029 g/ml HCl, 20.14 mmol) (25 ml) added to this solution. The reaction mixture was stirred at ambient temperature for 23 hours and the solvent removed under reduced pressure. The residue was triturated with ether and the suspension evaporated to dryness to give 1.86 g (quantitative yield); DEI-MS shows MW=229.

EXAMPLE 21

6-Amino-7-cyclohexyl-3,5-heptane diol hydrochloride ("Fast" isomer: 3-hydroxy center is either R or S, other centers are S, one of two diastereomers found in Example 3)

The fast isomer from Example 19 was treated as in Example 20 to give the analogous product; DEI-MS shows MW=229.

EXAMPLE 22

N-(4-Morpholinosulfonyl)-L-phenylalanyl-N-[1-(cyclohexylmethyl)-2,4-dihydroxyhexyl-L-N($\epsilon$)-(N-methylthiocarbamyl)]lysinamide ("Slow" isomer: 4-hydroxy center is either R or S, other centers are S)

To a 5° C. solution of the product from Example 20 (0.92 g, 3.47 mmol), the product from Example 18 (1.68 g, 3.47 mmol), HOBT (0.94 g, 6.95 mmol) and triethylamine (0.70 g, 3.47 mmol) in DMF (25 ml) was added DCC (0.72 g, 3.47 mmol). The reaction mixture was stirred at 5° C. for one hour, then at ambient temperature for 18 hours. The resulting suspension was filtered and the filtrate was evaporated at reduced pressure. The residue was purified by flash chromatography, eluting with 2 to 10% methanol in methylene chloride to give 1.48 g of product; FAB-MS shows MW=727.

EXAMPLE 23

N-(4-Morphoinosulfonyl)-L-phenylalanyl-N-[1-(cyclohexylmethyl)-2,4-dihydroxyhexyl-L-N($\epsilon$)-(N-methylthiocarbamyl)]lysinamide ("Fast" isomer: 4-hydroxy center is either R or S, other centers are S)

The product from Example 21 was coupled to the product from Example 18 as in Example 22 to give the desired compound; FAB-MS shows MW=727.

EXAMPLE 24

1-Cyclohexylmethyl)-4-(1,3-dithian-2-yl)-4-oxo-2-[(tetrahydro-2H-pyran-2-yl)oxy]butyl]carbamic acid, 1,1-dimethylethyl ester (pyran center is RS; others are S)

Preparation of anion of 1,3-dithiane: A solution of 12.4 g (0.10 mole) of 97% 1,3-dithiane in 200 ml of THF is cooled to −30° C. A quantity of 62.5 ml (0.1 mole) of 1.6M n-butyllithium is added with stirring under nitrogen over a period of 10 min ant −30°. After 15 min a solution of 42.0 g (0.011 mole) of 5-cyclohexylmethyl)-4-[(tetrahydro-2H-pyran-2-yl)oxy]-2-oxo-1-pyrrolidinecarboxylic acid, 1,1-dimethylethyl ester, mixture of [4S-[R*(R*), 5R*] and [4S-[4R*(S*), 5R*]] isomers, in 200 ml of THF is added to the above prepared 1,3-dithiane anion over a period of 10 min at −30°. The reaction solution is allowed to warm to room temperature over ca. 2 hours. After another hour at room temperature the solution is poured (under $N_2$) into a stirred mixture of 500 g of ice and water. Saturated citric acid solution (200 ml) and ether (600 ml) are added. The aqueous layer is separated and the organic phase is dried ($MgSO_4$), filtered and concentrated to give crude gum. Silica gel chromatography eluting with 1 to 30% EtOAc-Hexane gives 29.30 g (59%) of product as a gum; TLC (2:1 Hexane-EtOAc) major spot Rf 0.7, trace Rf 0.8. The product crystallizes and is recrystallized from EtOAc; mp 129°–131°; Cl-MS shows MW=501.

EXAMPLE 25

1-Cyclohexylmethyl)-4-(1,3-dithian-2-yl)-4-hydroxy-2-[(tetrahydro-2H-pyran-2-yl)oxy]butyl]carbamic acid, 1,1-dimethylethyl ester (pyran center and 4-hydroxy centers are RS; others are S).

A quantity of 0.70 g (0.014 mole) of ketone from Example 24 is dissolved in 150 ml of warm methanol. The cooled solution (25° C.) is treated with 1 ml of water and then a solution of 0.10 g (0.002 mole) of $KBH_4$ in 1 ml of water. After 1 hour acetone (5 ml) is added to the reaction solution. After 15 min the solvent is removed at reduced pressure, water (5 ml) is added and the separated gum is extracted into 20 ml of $CH_2Cl_2$. The solution is dried ($K_2CO_3$), filtered and concentrated to give crude product as a mixture of diastereomers; TLC (2:1 Hexane-EtOAc) 2 spots, Rf 0.3 and 0.5; FAB-MS shows MW=503.3.

EXAMPLE 26

2-Amino-1-cyclohexyl-5-(1,3-dithian-2-yl)-3,5-pentane diol (1S, 3S, 4S and 1R, 3S, 4S isomers)

A solution of 0.40 g (0.0008 mole) of the blocked amino diol from Example 25 in 20 ml of 50% MeOH—$CH_2Cl_2$ is cooled to 10° and saturated with HCl gas. The solution is allowed to warm to room temperature and to stand overnight. The solvent is stripped off at reduced pressure and the residue is dissolved in 5 ml of water. The solution is treated with activated charcoal, filtered, and saturated with solid $K_2CO_3$. The separated gum is extracted into EtOAc, and the organic layer is dried over $MgSO_4$ and evaporated; wt. 0.15 g of mixed diastereomers; TLC (1:10 MeOH—$CHCl_3$-saturated with $NH_3$) 2 spots, Rf 0.5 and 0.7; MS shows MW=320.1. Separation of diastereomers is accomplished by silica gel chromatography eluting with from 1 to 10% MeOH—$CHCl_3$, saturated with $NH_3$.

EXAMPLE 27

[1-(Cyclohexylmethyl)-6-(1-methylethyl)thio]-4-oxo-2-[tetra-hydro-2H-pyran-2-yl)oxy]hexyl]carbamic acid, 1,1-dimethyl-ethyl ester (pyran center is RS; others are S)

A solution of 20.50 g (0.05 mole) of the vinyl ketone from Example 9 in 100 ml of MeOH is treated with 5.70 g (0.075 mole) of isopropyl mercaptan and then 8.10 g (0.080 mole) of triethylamine. After 15 min at room temperature the solvent is removed at reduced pressure and 200 ml of cold saturated citric acid and 300 ml of 25% $CH_2CH_2$-ether are added to the residue. The dried ($MgSO_4$) extract is concentrated; wt. 21.00 g (86%); TLC (2:1 Hexane-EtOAc) one spot, Rf 0.8 (visualized with ninhydrin and heat);

Analysis, Calcd for $C_{26}H_{47}NO_5S$: C, 64.29; H, 9.75; N, 2.88; S, 6.60. Found: C, 65.08; H, 9.91; N, 2.76; S, 5.90.

EXAMPLE 28

[1-(Cyclohexylmethyl)-4-hydroxy-6-[(1-methylethyl)-thio]-2-[(tetrahydro-2H-pyran-2-yl)oxy]hexyl]carbamic acid, 1,1-dimethylethyl ester (pyran center and 4-hydroxy centers are RS; others are S)

Water (2 ml) is added to a solution of 2.80 g (0.0058 mole) of ketone from Example 27 in 20 ml of methanol. A solution of 0.31 g (0.0058 mole) of $KBH_4$ in 2 ml of water is added. After one hour at room temperature, 5 ml of acetone is added. The solvent is stripped off at reduced pressure. Ice water (10 ml) is added and the product is extracted into 50 ml of ether; wt. 2.58 g (91%); TLC (2:1 Hexane-EtOAc) one spot, Rf 0.55; FAB-MS shows MW=487.3.

EXAMPLE 29

2-Amino-1-cyclohexyl-7-[(1-methyethyl)thiol]-3,5-heptane diol (2S, 3S, 5S and 2S, 3S, 5R isomers)

A solution of 2.40 g (0.005 mole) of blocked amino diol from Example 28 in 50 ml of $CH_2Cl_2$ is treated with 25 ml of methanolic HCl (methanol saturated with HCl at 10°). After four hours at room temperature the volatiles are removed at reduced pressure and the residue is dissolved in 100 ml of water. The charcoaled solution is saturated with $K_2CO_3$ and the mixed diastereomers are extracted into 100 ml of 25% $CH_2Cl_2$-ether; wt. 0.70 g (47%); TLC (1:10 MeOH-$CHCl_3$-saturated with $NH_3$) two spots, Rf 0.4 and 0.5. Separation of diastereomers is accomplished by silica gel chromatography eluting with 2-5% MeOH-$CHCl_3$ (saturated with $NH_3$); Isomer A, TLC (above system) Rf 0.5; MS shows MW=303.2; Isomer B, TLC (above system) Rf 0.4; MS shows MW=303.2.

EXAMPLE 30

N-(4-Morpholinosulfonyl)-L-phenylalanyl-DL-(2-carboxymethyl)glycine; methyl ester Dimethyl aminomalonate was coupled to N-(4-morpholinosulfonyl)-Phe as described in Example 16. The product was crystallized from methyl, t-butyl ether; FAB-MS shows MW=443.

EXAMPLE 31

N-(4-Morpholinosulfonyl)-L-phenylalanyl-DL(2-carbomethoxy)glycine, dicyclohexylamine salt The product from Example 30 (10 g, 22.6 mmol) was dissolved in a mixture of THF (50 ml) and methanol (25 ml) and treated at 0° C. with 2N NaOH (23 ml, 46 mmol). After 15 min the reaction was quenched with 2N HCl (23 ml, 46 mmol) and partitioned between ethyl acetate and sat. NaCl$_{(aq)}$. The organic layer was dried over $MgSO_4$ and evaporated. The residue was redissolved in ethyl acetate (40 ml), treated at 0° C. with diisopropylamine (4.5 ml, 22.6 mmol) and allowed to stand at room temperature. The crystalline product was collected to give 12.9 g; MP 122-123.

EXAMPLE 32

N-(4-Morpholinosulfonyl)-L-phenylalanyl-N-[1-(cyclohexylmethyl)-2,4-dihydroxyhexyl]-DL-(2-carbomethoxy)glycinamide (4-hydroxy center is R or S; others are S) ("slow isomer")

The aminodiol.HCl from Example 20 was coupled with the dicyclohexylamine salt from Example 31 by treatment with DCC and HOBT in DMF. Work-up and chromatography was performed in a manner analogous to Example 22 to afford the desired product; FAB-MS shows MW=640.

EXAMPLE 33

1-Cyclohexylmethyl)-2,4-dihydroxyhexyl]-L-[N($\alpha$)-1,1-dimethylethoxy)carbonyl-2-(2-propenyl)]glycinamide (4-hydroxy center is R or S; others are S)("slow" isomer)

The aminodiol from Example 20 was coupled to BOC-ALG and purified in a manner analogous to Example 4 to give the product as a single stereoisomer; FAB-MS shows MW=426.

EXAMPLE 34

N-1-(Cyclohexylmethyl)-2,4-dihydroxyhexyl]-L-[2-(2-propenyl)]glycinamide (4-hydroxy center is R or S; others are S) ("slow" isomer)

The product from Example 33 was dissolved in dichloromethane and treated with methanolic HCl at RT for 1 hour. Evaporation afforded the desired product as its hydrochloride salt. The free base was regenerated by partitioning between ethyl acetate and dilute $K_2CO_3$.(aq). The organic layer was dried over $MgSO_4$ and evaporated to a foam; FAB-MS shows MW=326.

EXAMPLE 35

N-(4-Morpholinosulfonyl)-L-phenylalanyl-N-1-cyclohexylmethyl)-2,4-dihydroxyhexyl]-L-[2-(2-propenyl)]glycinamide (4-hydroxy center is R or S; others are S ("slow" isomer)

The product from Example 34 was coupled to N-(4-morpholinosulfonyl)-Phe in a manner analogous to Example 7 to give the desired product; FAB-MS shows MW=622.

EXAMPLE 36

N-[4-(1,1-Dimethylethoxycarbonyl)-1-piperazinosulfonyl]-L-phenylalanyl-N-[1-cyclohexylmethyl)-2,4-dihydroxyhexyl]-L-[2-(2-propenyl)]glycinamide (4-hydroxy center is R or S; others are S) ("slow" isomer)

The product from Example 34 was coupled to N-(4-BOC-1-piperazinosulfonyl)-PHE in a manner analogous to Example 7 to give this product; FAB-MS shows MW=721.

EXAMPLE 37

N-(1-Piperazinosulfonyl)-L-phenylalanyl-N-[1-(cyclohexylmethyl)-2,4-dihydroxyhexyl]-L-2-(2-propenyl)]glycinamide (4-hydroxy center is R or S; others are S) ("slow" isomer)

The product from Example 36 was dissolved in dichloromethane and treated with methanolic HCl to remove the BOC group. Evaporation of solvents and regeneration of the free base by partitioning between ethyl acetate and dilute $K_2CO_3$, drying the organic layer over $MgSO_4$, and evaporating the organic layer gives the product as a foam; FAB-MS shows MW=621.

EXAMPLE 38

N-(4-Morpholinosulfonyl)-L-phenylalanyl-N-[1-(cyclohexylmethyl)-2,4-dihydroxyhexyl]glycinamide (4-hydroxy center is R or S; others are S) ("slow" isomer)

N-(4-Morpholinosulfonyl)-L-phenalalanyl glycine was prepared in a manner analogous to Examples 30 and 31, substituting glycine ethyl ester for dimethyl aminomalonate. This material was subsequently coupled to the aminodiol from Example 20 in a manner analogous to Example 22 to afford the desired product; FAB-MS shows MW=582.

EXAMPLE 39

N-(4-Morpholinosulfonyl)-L-phenylalanyl-N-[1-(cyclohexylmethyl)-2,4-dihydroxy-6-[(1-methylethyl)thio]-DL-(2-carboxymethyl)-glycine. (4-hydroxy center is R or S; others are S) ("slow" isomers)

The aminodiol.HCl from Example 29 was coupled to the dicyclohexylamine salt from Example 31 by treatment with DCC and HOBT in DMF. Work-up and chromatography was performed in a manner analogous to Example 22 to afford the desired product; FAB-MS shows MW=696.

We claim:
1. A compound of the formula

A-X-Y-W    I or a pharmaceutically acceptable salt thereof wherein
A is

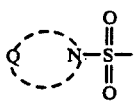

and X is Phe or Tyr(OMe);

Y is His, TZA, Alg, Lys (CSNHMe) or

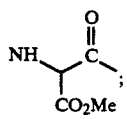

W is

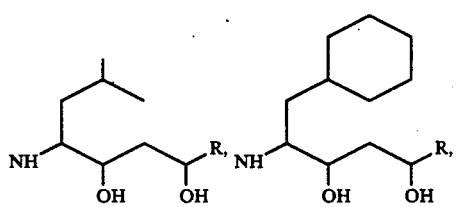

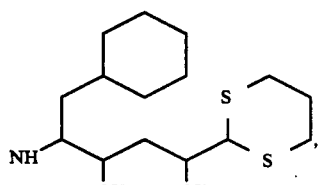

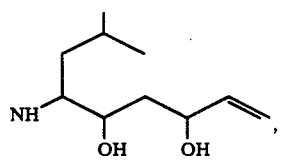

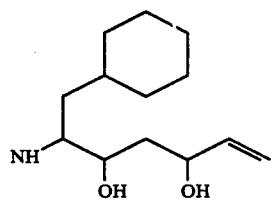

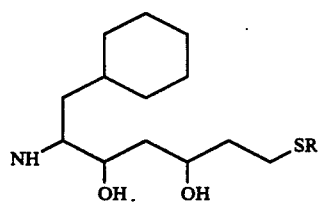

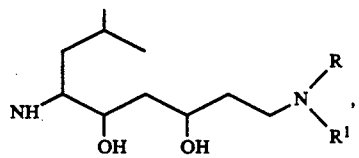

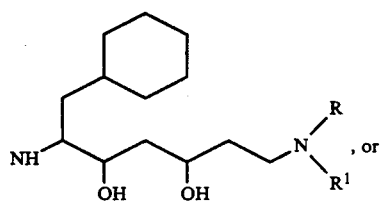, or

-continued
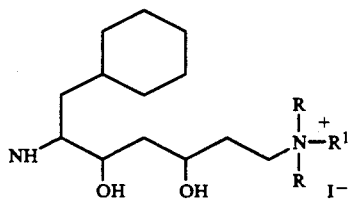
wherein R and R[1] are each independently $CH_3$ or $C_2H_5$,
is a saturated ring containing three or four carbon atoms and Q is O, N-BOC or NR with R as defined above.
2. A compound selected from the group consisting of:
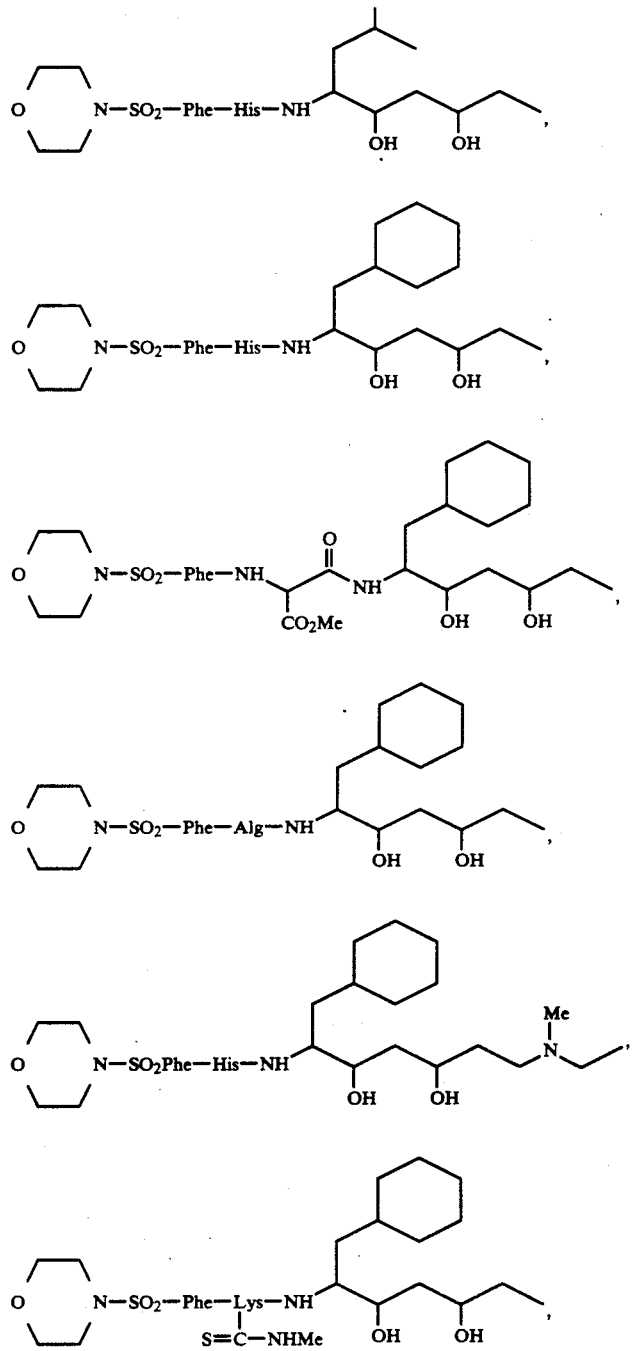

-continued
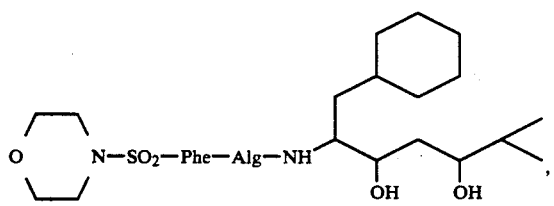
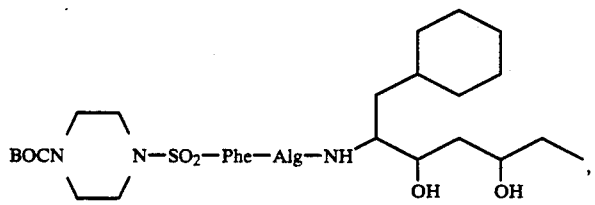
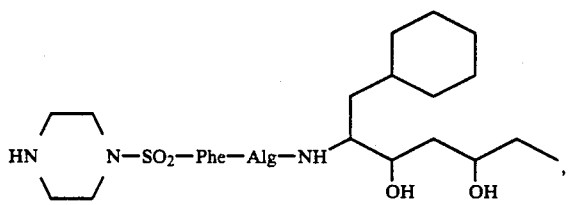
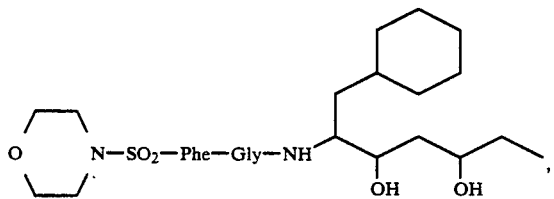
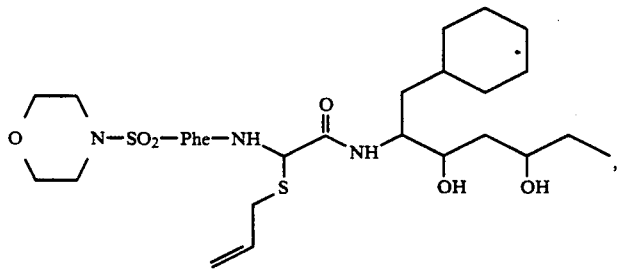
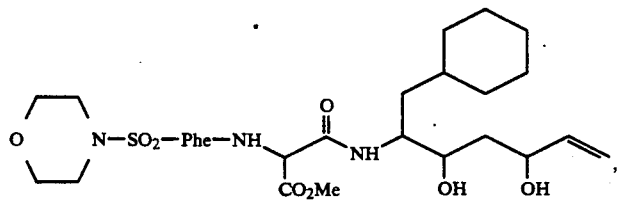
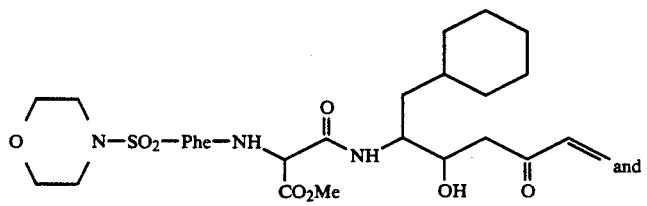
and -continued

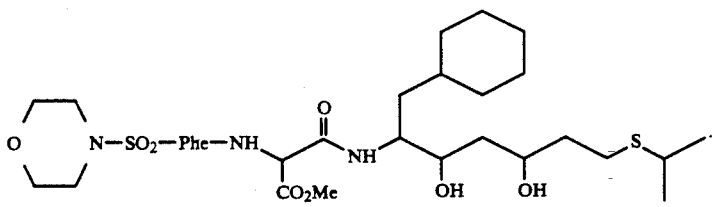

3. A pharmaceutical composition comprising a renin-inhibitory effective amount of a compound according to claim 1 together with a pharmaceutically acceptable carrier.

4. A method of treating renin-associated hypertension which comprises administering to a mammal an effective amount of a pharmaceutical composition according to claim 3.

5. A method of treating renin-associated hyperaldosteronism which comprises administering to a mammal an effective amount of a pharmaceutical composition according to claim 3.

6. A method of treating renin-associated congestive heart failure which comprises administering to a mammal an effective amount of a pharmaceutical composition according to claim 3.

7. A method of determining the presence of renin-associated hypertension in a patient which comprises administering to said patient, at a hypotensive dosage level and as a single dose an effective amount of, a peptide of claim 1, followed by monitoring of said patient's blood pressure.

* * * * *